US011612338B2

(12) United States Patent
Auerbach

(10) Patent No.: US 11,612,338 B2
(45) Date of Patent: Mar. 28, 2023

(54) BODY MOTION MONITOR

(71) Applicant: BreatheVision Ltd., Kibbutz Yad Mordechai (IL)

(72) Inventor: Ditza Auerbach, Aseret (IL)

(73) Assignee: BreatheVision Ltd., Nes Ziona (IL)

( * ) Notice: Subject to any disclaimer, the term of this patent is extended or adjusted under 35 U.S.C. 154(b) by 1131 days.

(21) Appl. No.: 16/095,431

(22) PCT Filed: Apr. 21, 2017

(86) PCT No.: PCT/IL2017/050466
§ 371 (c)(1),
(2) Date: Oct. 22, 2018

(87) PCT Pub. No.: WO2017/183039
PCT Pub. Date: Oct. 26, 2017

(65) Prior Publication Data
US 2019/0133499 A1 May 9, 2019

Related U.S. Application Data

(63) Continuation-in-part of application No. 15/135,797, filed on Apr. 22, 2016, now Pat. No. 9,788,762.
(Continued)

(51) Int. Cl.
A61B 5/11 (2006.01)
A61B 5/113 (2006.01)
(Continued)

(52) U.S. Cl.
CPC .......... A61B 5/1135 (2013.01); A61B 5/0077 (2013.01); A61B 5/02444 (2013.01);
(Continued)

(58) Field of Classification Search
None
See application file for complete search history.

(56) References Cited

U.S. PATENT DOCUMENTS 4,836,219 A 6/1989 Hobson et al.
6,306,088 B1 * 10/2001 Krausman .......... A61B 5/02055
600/534
(Continued)

FOREIGN PATENT DOCUMENTS

WO   WO 01/76467      10/2001
WO   WO 2004/049109   6/2004
(Continued)

OTHER PUBLICATIONS

Supplementary European Search Report and the European Search Opinion dated Nov. 5, 2019 From the European Patent Office Re. Application No. 17785579.8. (10 Pages).
(Continued)

Primary Examiner — Ankit D Tejani

(57) ABSTRACT

A system for monitoring the respiratory activity of a subject, which comprises one or more movement sensors, applied to the thorax of a subject, for generating first signals that are indicative of movement of the thorax of the subject; a receiver for receiving the first generated signals during breathing motion of the subject; and one or more computing devices in data communication with the receiver, for analyzing the breathing motion. The computing device is operable to generate a first breathing pattern from the first signals; divide each respiratory cycle experienced by the subject and defined by the first pattern into a plurality of portions, each of the portions delimited by two different time points and calculate, for each of the plurality of portions of a given respiratory cycle of the first pattern, a slope representing a thorax velocity; derive, from the given respiratory cycle of the first pattern, a pulmonary air flow rate of the
(Continued)

subject during predetermined portions of the respiratory cycle; compare between corresponding portions of the first pattern and average flow rates during different phases of the breathing cycle, to calibrate a thorax velocities of the subject with pulmonary air flow rates; and determine respiratory characteristics of the subject for subsequent respiratory cycles experienced by the subject, based on a calculated thorax velocity and the calibration.

20 Claims, 12 Drawing Sheets

Related U.S. Application Data which is a continuation-in-part of application No. PCT/IL2014/050916, filed on Oct. 22, 2014.

(60) Provisional application No. 62/020,649, filed on Jul. 3, 2014, provisional application No. 61/895,000, filed on Oct. 24, 2013.

(51) Int. Cl.
| | |
|---|---|
| A61B 5/00 | (2006.01) |
| A61B 5/08 | (2006.01) |
| A61B 5/024 | (2006.01) |
| A61B 5/087 | (2006.01) |
| A61B 5/091 | (2006.01) |
| A61B 90/00 | (2016.01) |
| A61B 3/113 | (2006.01) |
| A61B 17/00 | (2006.01) |

(52) U.S. Cl.
CPC ............ *A61B 5/087* (2013.01); *A61B 5/0816* (2013.01); *A61B 5/091* (2013.01); *A61B 5/1101* (2013.01); *A61B 5/1114* (2013.01); *A61B 5/1127* (2013.01); *A61B 5/1128* (2013.01); *A61B 5/4812* (2013.01); *A61B 5/4818* (2013.01); *A61B 5/7282* (2013.01); *A61B 3/113* (2013.01); *A61B 5/1117* (2013.01); *A61B 5/6898* (2013.01); *A61B 5/7257* (2013.01); *A61B 90/39* (2016.02); *A61B 2017/00699* (2013.01); *A61B 2090/3983* (2016.02); *A61B 2503/04* (2013.01); *A61B 2560/0238* (2013.01); *A61B 2562/0219* (2013.01)

(56) References Cited

U.S. PATENT DOCUMENTS

| | | | |
|---|---|---|---|
| 6,351,662 | B1 | 2/2002 | Franck et al. |
| 6,352,517 | B1 | 3/2002 | Flock et al. |
| 6,937,696 | B1 | 8/2005 | Mostafavi |
| 6,997,882 | B1 | 2/2006 | Parker et al. |
| 8,527,217 | B2 | 9/2013 | Moodie |
| 2002/0188194 | A1 | 12/2002 | Cosman |
| 2003/0100843 | A1 | 5/2003 | Hoffman |
| 2005/0201509 | A1 | 9/2005 | Mostafavi et al. |
| 2007/0016009 | A1 | 1/2007 | Lakin et al. |
| 2008/0287728 | A1 | 11/2008 | Mostafavi et al. |
| 2009/0305212 | A1 | 12/2009 | McKenzie et al. |
| 2010/0183196 | A1 | 7/2010 | Fu et al. |
| 2011/0015521 | A1 | 1/2011 | Faul |
| 2011/0046499 | A1 | 2/2011 | Klewer et al. |
| 2011/0144517 | A1 | 6/2011 | Cervantes |
| 2012/0179005 | A1 | 7/2012 | McCool |
| 2013/0018232 | A1 | 1/2013 | D'Souza et al. |
| 2013/0030257 | A1 | 1/2013 | Nakata et al. |
| 2013/0172769 | A1 | 7/2013 | Arvind et al. |
| 2014/0070957 | A1* | 3/2014 | Longinotti-Buitoni ..................... A61B 5/02055 340/870.01 |
| 2014/0228657 | A1 | 8/2014 | Palley et al. |
| 2014/0249430 | A1* | 9/2014 | Sims .................... A61B 5/1135 600/534 |
| 2015/0073281 | A1 | 3/2015 | Mestha et al. |
| 2015/0164380 | A1 | 6/2015 | O'Dwyer et al. |
| 2015/0257699 | A1 | 9/2015 | Bjerrum |
| 2016/0029949 | A1 | 2/2016 | Landesberg et al. |
| 2016/0235344 | A1 | 8/2016 | Auerbach |
| 2017/0367625 | A1 | 12/2017 | Auerbach |

FOREIGN PATENT DOCUMENTS

| | | |
|---|---|---|
| WO | WO 2006/005021 | 1/2006 |
| WO | WO 2006/047400 | 5/2006 |
| WO | WO 2009/011643 | 1/2009 |
| WO | WO 2015/059700 | 4/2015 |
| WO | WO 2017/183039 | 10/2017 |

OTHER PUBLICATIONS

Fekr et al. "Design and Evaluation of An Intelligent Remote Tidal Volume Variability Monitoring System in E-Health Applications", IEEE Journal of Biomedical and Health Informatics, XP011667701, 19(5): 1532-1548, Published Online Jun. 16, 2015.
Corrected Notice of Allowability dated Jul. 21, 2017 From the US Patent and Trademark Office Re. U.S. Appl. No. 15/135,797. (6 Pages).
International Preliminary Report on Patentability dated Mar. 13, 2016 From the International Preliminary Examining Authority Re. Application No. PCT/IL2014/050916. (18 Pages).
International Preliminary Report on Patentability dated Nov. 1, 2018 From the International Bureau of WIPO Re. Application No. PCT/IL2017/050466. (10 Pages).
International Search Report and the Written Opinion dated Jul. 27, 2017 From the International Searching Authority Re. Application No. PCT/IL2017/050466. (15 Pages).
International Search Report and the Written Opinion dated Jan. 29, 2015 From the International Searching Authority Re. Application No. PCT/IL2014/050916. (26 Pages).
Notice of Allowance dated Apr. 10, 2017 From the US Patent and Trademark Office Re. U.S. Appl. No. 15/135,797. (23 Pages).
Supplementary European Search Report and the European Search Opinion dated Jun. 16, 2017 From the European Patent Office Re. Application No. 14856467.7. (8 Pages).
Allen "Learning Body Shape Models From Real-World Data", A Dissertation Submitted in Partial Fulfillment of the Requirements for the Degree of Doctor of Philosophy, University of Washington, Graduate School, Seattle, Washington, USA, p. 1-107, 2005.
DeMenthon et al. "Model-Based Object Pose in 25 Lines of Code", International Journal of Computer Vision, XP002513566, 15(1): 123-141, Jan. 1995.
Enochson et al. "Programming and Analysis for Digital Time Series Data", The Shock and Vibration Information Center, United States Department of Defense, p. 142, 1968.
Ernst et al. "Correlation Between External and Internal Respiratory Motion: A Validation Study", International Journal of Computer Assisted Radiology and Surgery, XP035050195, 7(3): 483-492, Published Online Aug. 19, 2011. Abstract, Sections 'Introduction', 'Methods and Materials', Figs. 1-5.
Horn "Obtaining Shape From Shading Information", The Psychology of Computer Vision, Chap.4: 115-155, 1975.
Lucas et al. "An Iterative Image Registration Technique With An Application to Stereo Vision", Proceedings of the 7th International Joint Conference on Artificial Intelligence, IJCAI, Vancouver, British Columbia, Canada, Aug. 24-28, 1981, p. 674-679, Aug. 24, 1981, Proceedings of the DARPA Image Understanding Workshop, p. 121-130, Apr. 1981.
McClelland et al. "Respiratory Motion Models: A Review", Medical Image Analysis, XP055106223, 17(1): 19-42, Available Online Oct. 8, 2012.

(56) References Cited

OTHER PUBLICATIONS

Rubinstein et al. "Dictionaries for Sparse Representation Modeling", Proceedings of the IEEE, 98(6): 1045-1057, Apr. 22, 2010.
Scharstein et al. "A Taxonomy and Evaluation of Dense Two-Frame Stereo Correspondance Algorithms", International Journal of Computer Vision, 47(1/2/3): 7-42, Apr. 2002.
Scholkopf et al. "Estimating the Support of A High-Dimensional Distribution", Neural Computation, 13(7): 1443-1471, Jul. 2001.
Scholkopf et al. "Learning With Kernels: Support Vector Machines, Regularization, Optimization, and Beyond (Adaptive Computation and Machine Learning)", MIT Press, 2 P., Dec. 2001.
Vision Caltech "Camera Calibration Toolbox for Matlab: Fifth Calibration Example—Calibrating A Stereo System, Stereo Image Rectification and 3D Stereo", Vision Caltech, Retrieved From the Internet, 3 P., Oct. 20, 2017.
Requisition by the Examiner dated Oct. 6, 2021 From the Innovation, Science and Economic Development Canada, Canadian Intellectual Property Office Re. Application No. 2,928,312. (7 Pages).
Faithful et al. "Measurement of the Relative Contributions of Rib Cage and Abdomen/diaphragm to Tidal Breathing in Man", British Journal of Anaesthesia, 51(5):391-398, May 1979.
Requisition by the Examiner dated Nov. 27, 2020 From the Innovation, Science and Economic Development Canada, Canadian Intellectual Property Office Re. Application No. 2,928,312. (4 Pages).
Invitation Pursuant to Rule 137(4) EPC and Article 94(3) EPC dated Oct. 20, 2021 From the European Patent Office Re. Application No. 14856467.7 (3 Pages).
Office Action dated Dec. 6, 2020 From the Israel Patent Office Re. Application No. 245185 and Its Translation Into English. (7 Pages).
Restriction Official Action dated Feb. 11, 2019 From the US Patent and Trademark Office Re. U.S. Appl. No. 15/682,093. (10 pages).
Requisition by the Examiner dated Jul. 28, 2022 From the Innovation, Science and Economic Development Canada, Canadian Intellectual Property Office Re. Application No. 2,928,312. (5 Pages).

\* cited by examiner

BODY MOTION MONITOR

FIELD OF THE INVENTION

The present invention relates to monitoring apparatus. More particularly, the invention relates to sensor-based monitoring apparatus for monitoring a variety of activities, such as human breathing.

BACKGROUND OF THE INVENTION

Respiration rate is a vital sign that is monitored either intermittently or continuously in a variety of situations, including but not limited to during and after medical intervention procedures. Continuous monitoring apparatus can be placed in contact with the body (abdominal belts or air flow measuring devices with a mask or invasive flow devices placed inside the trachea) or non-contact (e.g. pressure sensors under mattress, or a Doppler sensor). Continuous monitoring of respiration beyond the respiratory rate (such as breathing patterns, breathing depth, accurate minute ventilation and apnea) is achieved nowadays using contact and invasive sensors.

SUMMARY OF THE INVENTION

The present invention relates to a system for non-invasive monitoring of the respiration properties through sensing chest wall movements. Various measures are deduced such as respiratory rate, respiratory effort, tidal volumes and respiratory patterns. These properties are obtained under a wide range of ambient conditions such as in the presence of subject's non-breathing movements, subject pose changes, various ambient lighting conditions, physical obstructions, etc. In addition reliable early warnings can be issued based on such respiratory properties and based on analysis of the sensor signals such as image sensors and inertial sensor signals. The term "subject", as used herein, is meant to indicate an individual the respiratory activity of whom is being tracked, whether a patient in a health facility, or a person being tested for any reason or purpose.

The system is applicable to various settings such as monitoring subjects who are undergoing sedative or pain killing treatment that can depress respiration, monitoring deterioration in the critically ill, monitoring infants to protect against SIDS and diagnostic tools for sleep testing such as for sleep apnea. In such cases, the monitor of the invention can be used to track other movements in addition to respiratory movements, e.g., leg movements and eye movements, as well as for quantifying awakenings and sedation level. These can be important for sleep staging analysis.

Another use of the invention is for the diagnosis of conditions using intermittent monitoring or comparison of measurements taken at different times. One example of this is comparison of breathing movement patterns of the chest and abdomen before and after surgery in order to diagnose diaphragm paralysis. Also, change in respiration patterns at rest over time can be tracked with the system of the invention.

The settings in which the system may be used are versatile such as hospitals, clinics, home, battlefield and even outdoor environments. Often for some of these conditions, low respiratory rate is a late indicator of respiratory distress, and other measures such as the depth of breath and pulmonary motion patterns are earlier indicators of deterioration. There are situations in which the respiratory rate is not a sufficient differentiator of deterioration as in the case of an airway obstruction.

Often in these settings, the subject does not stand still and a variety of disturbances may occur such as changing subject pose, chest wall motion whose source is not associated with breathing and possible movement of a marker attached to the subject relative to the chest wall. The present invention enables respiratory monitoring in the presence of these disturbances.

In one aspect, the present invention is directed to a system for monitoring the respiratory activity of a subject, which comprises:
 a) one or more movement sensors, applied to the thorax of a subject, for generating first signals that are indicative of movement of the thorax of the subject;
 b) a receiver for receiving the first generated signals during breathing motion of the subject; and
 c) one or more computing devices in data communication with the receiver, for analyzing the breathing motion, wherein the one or more computing devices is operable to:
  i. generate a first breathing pattern from the first signals;
  ii. divide each respiratory cycle experienced by the subject and defined by the first pattern into a plurality of portions, each of the portions delimited by two different time points and calculate, for each of the plurality of portions of a given respiratory cycle of the first pattern, a slope representing a thorax velocity;
  iii. derive, from the given respiratory cycle of the first pattern, a pulmonary air flow rate of the subject during predetermined portions of the respiratory cycle;
  iv. compare between corresponding portions of the first pattern and average flow rates during different phases of the breathing cycle, to calibrate a thorax velocities of the subject with pulmonary air flow rates; and
  v. determine respiratory characteristics of the subject for subsequent respiratory cycles experienced by the subject, based on a calculated thorax velocity and the calibration.

The respiratory characteristics of the subject may be updated, based on the detection of changes in poses and/or the location of one or more markers with respect to the subject body.

The system may further comprise one or more additional movement sensors applied to the body of the subject, for generating third signals that are indicative of movement of the abdomen of the subject, wherein the receiver is configured to additionally receive the third generated signals during breathing motion of the subject and the one or more computing devices is also operable to generate a third breathing pattern from the third signals and to divide each respiratory cycle experienced by the subject and defined by the third pattern into a plurality of portions, such that a portion of the third pattern is delimited by the same two time points as a corresponding portion of the first pattern.

The one or more computing devices may be also operable to calculate, for each of the plurality of portions of a given respiratory cycle of the third pattern, a slope representing a body velocity and to determine respiratory characteristics of the subject for subsequent respiratory cycles experienced by the subject based on a calculated body velocity and thorax velocities.

The system may further comprise an alarming device in data communication with the one or more computing devices, wherein the one or more computing devices is also operable to command the alarming device to generate an alert if the markers movement with respect to the subject body exceeds a predetermined threshold.

The one or more computing devices may be also operable to readjust the calibration of the thorax velocity with the pulmonary air flow rate if the calculated changes in the 3-D position during the course of a breathing motion measuring operation.

The system may further comprise a one or more straps for attaching the one or more movement sensors to the subject's body, to facilitate performance of a breathing motion measuring operation while the subject is disposed on his or her side.

In one aspect, each of the one or more movement sensors and the one or more additional movement sensors may be an accelerometer, a gyroscope, or a combination thereof.

Each of the one or more movement sensors and the one or more additional movement sensors may be disposable and holds power supply elements and operating circuitry.

Each of the one or more movement sensors may be provided with an adhesive and is suitable to be positioned directly on the subject's thorax, and each of the one or more additional movement sensors is provided with an adhesive and is suitable to be positioned directly on the subject's abdomen.

Each of the one or more movement sensors may be positionable on a fabric located in close proximity to the subject's thorax, and is further provided with fastening means adapted to maintain it in a desired positional relationship to a chosen location on the subject's thorax, and wherein each of the one or more additional movement sensors is positionable on a fabric located in close proximity to the subject's abdomen, and is further provided with fastening means adapted to maintain it in a desired positional relationship to a chosen location on the subject's abdomen.

The one or more computing devices may be provided with communication apparatus suitable to deliver raw or analyzed data to a remote device.

The determined respiratory characteristics may include tidal volume calculation.

The present invention is also directed to a system for monitoring the respiratory activity of a subject, which comprises:
  a) one or more signal generating elements being movement sensors, applied to the thorax of a subject, for generating signals that are indicative of movement of the thorax of the subject;
  b) a receiver for receiving the generated signals during breathing motion of the subject; and
  c) one or more computing devices in data communication with the receiver, for analyzing the breathing motion, wherein the one or more computing devices is operable to:
    i. calculate, in response to the received generated signals, a magnitude of a maximum displacement in 3D space of the one or more signal generating elements during a cycle of the breathing motion;
    ii. calculate the magnitude of a current displacement in 3D space of the one or more signal generating elements during the breathing motion with respect to a reference tidal volume associated with the maximum displacement in 3D space;
    iii. compare current and maximum displacements; and
    iv. calculate the tidal volume based on a calibration between the current and maximum displacements.

Each of the one or more kinematic signal generating elements may be an accelerometer, a gyroscope, or a combination thereof.

In one aspect:
  each of the signal generating elements is disposable and holds power supply elements and operating circuitry;
  each of the signal generating elements is provided with an adhesive and is suitable to be positioned directly on the subject's thorax;
  each of the signal generating elements is positionable on a fabric located in close proximity to the subject's thorax, and is further provided with fastening means adapted to maintain it in a desired positional relationship to a chosen location on the subject's thorax; or
  each of the signal generating elements is connectable to a base attached directly to the subject's thorax, wherein a fabric is located between the base and the signal generating element.

The signal generating elements may include a first group of one or more kinematic signal generating elements selected from an accelerometer, a gyroscope, or a combination thereof, and a second group of signal generating elements including one or more light sources or one or more light source assemblies, each of which comprises one two or more spaced light sources suitable to generate light, which are mounted on a rigid plate and fed by a power source, and the receiver is a stationary camera for tracking movement of, and imaging, the two or more light sources during breathing motion of the subject, the one or more computing devices operable to calculate the magnitude of a maximum displacement and of a current displacement in conjunction with both the first and second group of signal generating elements.

The one or more computing devices may be also operable to output an alert when a current tidal volume for a monitored respiration cycle deviates from the reference tidal volume by more than a predetermined threshold that is indicative of an anomalous breathing pattern.

The system may be provided with communication apparatus suitable to deliver raw or analyzed data to a remote device.

The present invention is also directed to a sleep assessment system, which comprises:
  a) one or more movement sensors adhesively applied to an eyelid of a subject, for generating signals that are indicative of movement of the eyelid, wherein each of the movement sensors comprises operating circuitry and a wireless transmitter for transmitting the generated signals;
  b) a receiver for receiving the generated signals; and
  c) a computing device in data communication with the receiver, which is operable to analyze the generated signals, calculate a movement pattern of the eyelid during sleep, and to associate the calculated movement pattern with a known sleep stage.

DETAILED DESCRIPTION OF THE INVENTION

Figure 1:
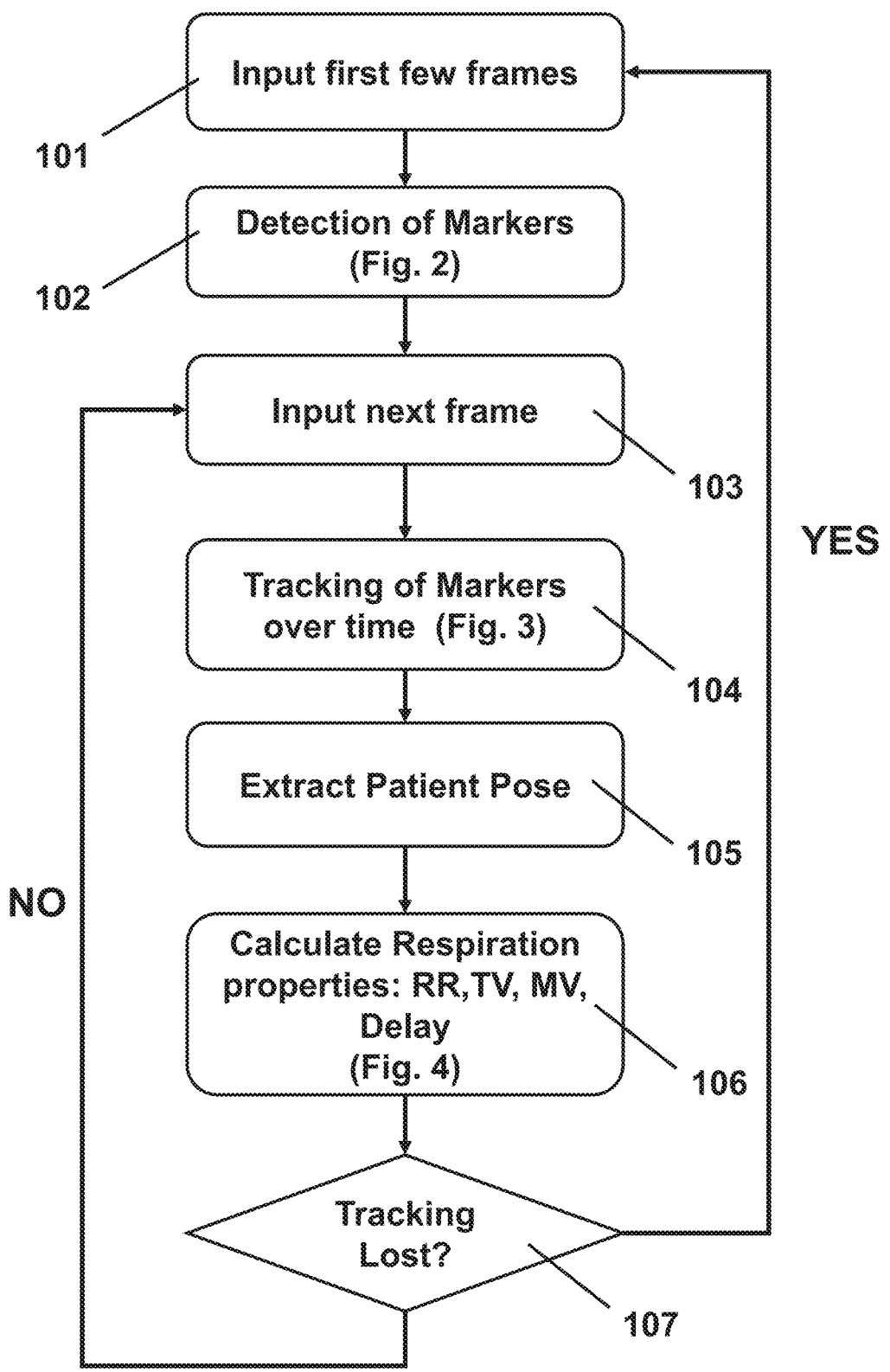
FIG. 1 is a flow chart of a monitoring stage, according to one embodiment of the invention.

The invention will be described below with reference to illustrative embodiments, which are not meant to limit its scope but are only meant to assist the skilled person to understand the invention and its uses. While in some cases reference may be made to a single subject or to a single marker, or to a specific number of markers, it should be understood that this is done for the sake of simplicity but the invention is not limited to the monitoring of a single subject and more than one subject can be monitored simultaneously by a single system of the invention. Similarly, different numbers of markers can be used, as will be further discussed below, which can be positioned at different locations, depending on the result that it is desired to obtain.

The following description relates to a system for monitoring the respiratory activity of a subject in a static position such as in bed, but it will be appreciated that it may also be used to monitor the respiratory activity of a moving subject, particularly one that is undergoing physical activity, such as riding a bicycle.

Exemplary System Overview

An illustrative system according to one embodiment of the invention consists of the following components:

1. One or more markers on the subject comprising signal generating elements, power supply elements and circuitry for operating the signal generating elements, either directly contacting the subject or on the subject's clothing or covers (i.e., on the sheets and/or blankets). These markers may include light emitting elements or inertial measuring sensors such as an accelerometer or a gyroscope. The markers may also include a microprocessor for performing some signal processing of the sensors.

2. A receiver for receiving the generated signals, for example an imaging device, which can be for example a CMOS video camera, a 3D camera, a thermal imager, a light field camera or a depth camera. The imaging device may have an associated illumination source such as IR LEDs in some embodiments. The receiver may also be configured with a wireless or wired electronic circuit to which a single or several inertial measurement sensors on the markers transmit measurements.

3. A computing device that is connected either wirelessly or wired to the receiver. The computing device may be remote and the connection to it may include an internet connection. As an example, part or all of the signal or image processing may be performed on a device such as a microprocessor or a computer board wired to the receiver. From there, a Bluetooth connection (or a connection of functionally similar technology) may connect to a gateway device that uploads the data to a cloud on the internet, or delivers it to a remote location, for further processing and storage.

4. An optional alarming device that issues either an audible or other kind of warning near the subject or to a remote location through a wired or wireless connection from the computing device.

5. An optional remote application, e.g., at a central nurse station or on a mobile device that can be used to control the signal generating element in the subject's vicinity and receive data from the signal generating element. For example, the remote application can be used to stream raw video or analyzed video from the receiver or signal generating element, once an alert is issued.

6. An optional display device that may be connected with a wired or wireless connection to the computing device.

The system may also comprise:

a. Additional signal generating elements, such as acoustic or other sensors that are either on the markers or connected to the computing device, e.g., a pulse oximeter.

b. Data storage devices, which can be located on the receiver, on a computing device or at a remote location, for storing data such as an electronic medical file. In addition, a database which includes training data for learning method parameters can be located on a computing device.

c. A spirometer or respirometer which measures a subject's air flow for calibration purposes in some embodiments and which may comprise means for generating signals that are indicative of the measured air flow and means for transmitting the generated signals to the computing device.

Subject Monitoring Process

Figure 12:
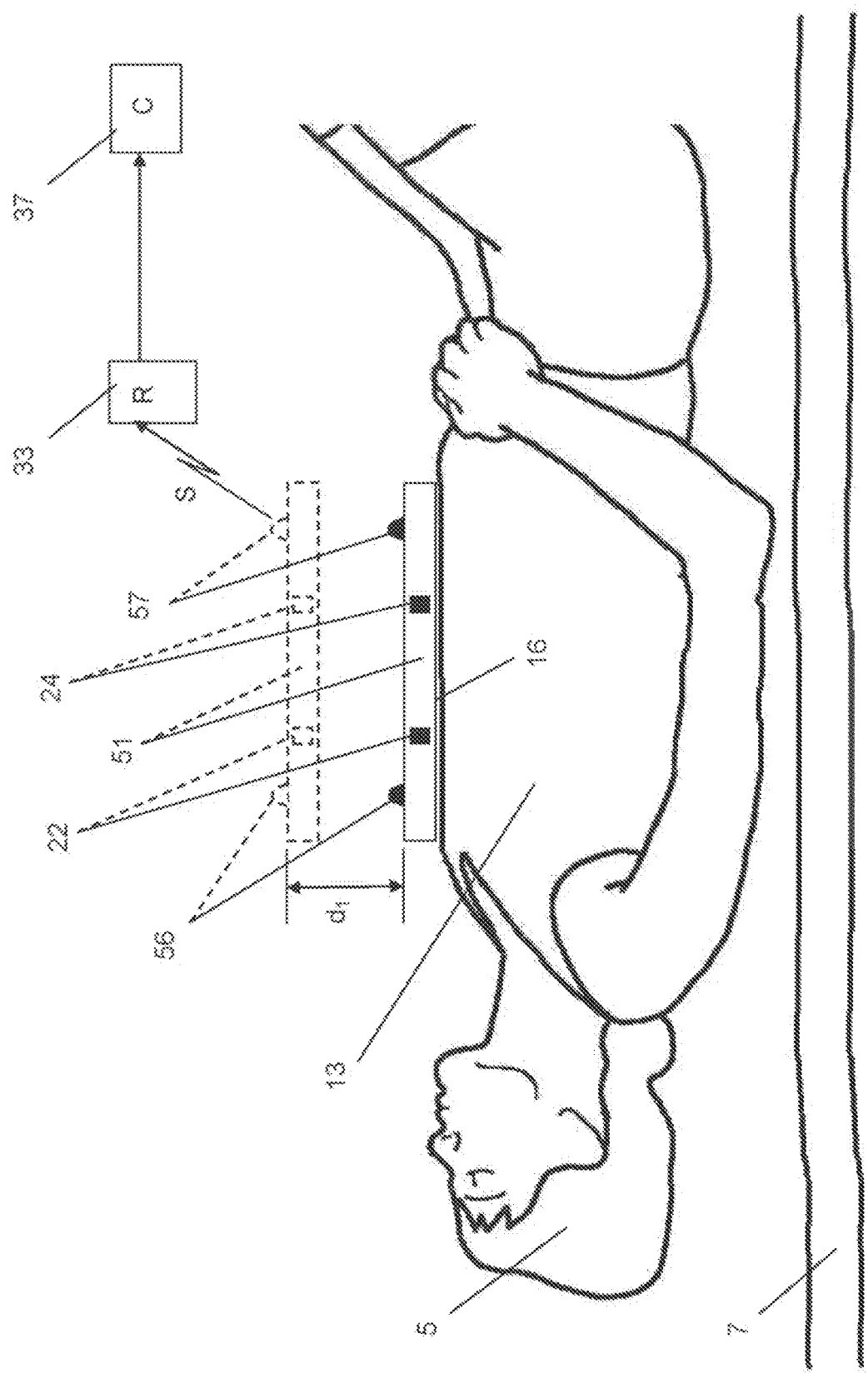
FIG. 12 is a schematic illustration of a system for monitoring the breathing patterns of a subject using inertial sensors.

Inertial Sensors:

The subject monitoring process is carried out according to one embodiment of the invention when a subject 5 in supine position is lying on a bed or on any other substantially horizontal support surface 7, as illustrated in FIG. 12.

A rigid marker 51 provided with two inertial or kinematic sensors 56 and 57, a single inertial sensor or any other suitable number thereof, such as a three-axis accelerometer and a 3-axis gyroscope, or a combination thereof, is used to calculate the respiratory activity of subject 5. Marker 51 is applied to the thorax 13 of subject 5 by engaging means 16, such as an adhesive connection applied directly to a bodily portion or an interfacing element such as a fabric in engagement with the thorax, to define a desired positional relationship to a chosen location on the subject's thorax. Each inertial sensor may be equipped with its own power supply element 22 and operating circuitry 24, or alternatively marker 51 has common power supply elements 22 and operating circuitry 24 for all inertial sensors provided therewith.

Figure 13:
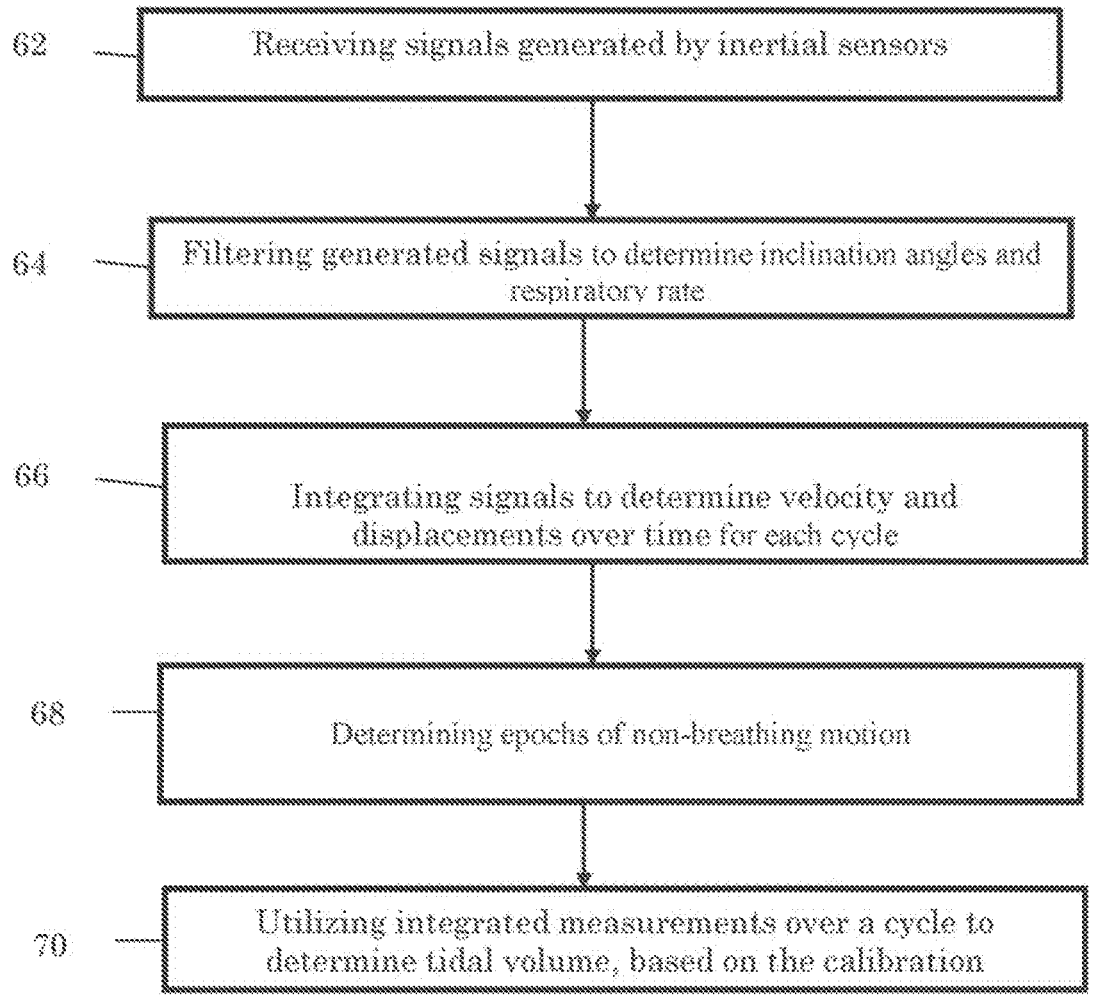
FIG. 13 is a method for determining the respiratory activity of a subject according to one embodiment of the invention.

During breathing motions, thorax 13 is displaced cyclically in 3D space. Marker 51 is also displaced by a distance of d1 in 3D space in response to the thorax displacement. Inertial sensors 56 and 57, as they are displaced, sense the force applied by thorax 13 during a breathing motion along a local inertial frame defined by their rectilinear structure, and in turn output a signal S that is indicative of the detected force or of the acceleration related to the detected force. Output signal S is generally a wireless signal, but may also be transmitted by a wired connection. Receiver 33, which is located in the proximity of marker 51 when the generated signal is a wireless signal but which also may be remotely separated from the marker, receives the generated signals S and transmits them to a computing device 37, which processes the generated signals S to calculate a sensor acceleration. Alternatively, the receiver 33 may be wired and located in close proximity to the computing device. Both of them may be situated on or near the patient's bed. The motion of the rigid marker 51 in a single exhalation or inhalation movement may be approximated as a 3D translation. However, it was found that there is a measurable rotation of the marker 51 of the order of 1 degree, depending on the subject and his pose. The acceleration due to the motion of the rigid marker 51 is sufficiently small that its inclination to gravity can be continuously estimated from a 3-axis accelerometer. This can be a achieved by calculating the Euler angles of marker 51 continuously and applying Kalman filtering to reduce noise. During breathing, the Euler angles were found to show a cyclic behaviour at the respiratory rate, thus providing an independent measurement of the respiratory rate. At times when the acceleration due to the marker's motion is non-negligible, a gyroscope 56 can be used in conjunction with the accelerometer in order to determine the acceleration of the marker in a global frame of reference using well-known navigation filtering techniques (see for example Quaternion-Based Extended Kalman Filter for Determining Orientation by Inertial and Magnetic Sensors, A. M. Sabatini, IEEE Trans. Biomed. Eng., 53 (2006). The global acceleration measurements can be integrated to determine the flow rates during each respiratory cycle, FIG. 13 illustrates a method for calculating a subject's respiratory rate and/or current tidal volume using the signals generated by the inertial sensors. After the computing device receives the signals generated by the inertial sensors in step 62, each signal is filtered in step 64 to determine the continuous rotational component of the breathing motion and subsequently the respiratory rate. In step 66, filtering is carried out to determine the acceleration due to breathing motion in a fixed global frame of reference which can in turn be integrated. In order to reduce integration error, the integration is carried out between peaks and troughs of single breaths by enforcing regularization constraints such as zero velocity at peaks and troughs of the respiratory signal. In step 68 non-breathing motion may be identified according to the presence of significant rotations in the signal related data; a possible criterion is that the cumulative angle of rotation over a predetermined period of time, e.g., the previous 10 seconds, increases compared to baseline values. In step 70, the learned calibration model is utilized using the, integrated measurements over a cycle in order to determine tidal volume.

Image Sensor:

Another embodiment of the monitoring process is carried out by imaging.

The imaging system of this particular embodiment of the invention consists of the following components:

1. Sensors and Illumination: One or more video cameras are used to record a scene of the subject. One example is a CMOS camera with night-vision capabilities, i.e. one in which a filter exists to filter out the visible light and sense the near IR optical wavelengths (NIR: 0.75-1.4 µm). There may also be ambient infrared LED illumination to increase ambient light if it is low. The ambient light source may be on the camera or in a chosen spatial arrangement in the subject's vicinity. Another example for the camera sensor is a thermal camera which is sensitive to mid-wavelength (3-8 µm) or long-wavelength (8-14 µm) infrared radiation. It too can have a light source such as a halogen lamp source which is used in Thermal Quasi-Reflectography. The sensor may also be a 3D depth camera such as the Realsense camera by Intel corporation.

2. Markers: Markers are applied either directly to the subject's body or integrated to a covering of the subject such as his clothing, his blanket, an elastic strap, or a bandage for example. The markers can be for example patches made from retro-reflective material, geometric patterns on the blanket or nightgown, or low voltage LED lights embedded or attached to clothing or patches. Each LED light can be either fixed or can flash each with its own known temporal pattern. Also, their light emitting wavelength and illumination may be specific for each LED. In order to enhance the outward facing light of these active markers, they can be embedded in retro reflective cones or other shaped contraptions made of reflective materials. Also the illumination angle may be narrow by using a lens. One specific marker, which is an object of the present invention and which can be used in a system such as this illustrative system, will be described in greater details later in this description.

Several markers may be incorporated together such as into an adhesive linear strip, or a 3D shape such as a dome shape consisting of scattered markers on its curved surface. Another possibility is to attach the marker assembly to elastic straps or a vest that the subject can wear and that reflect the thoracic movements.

In one embodiment of the invention the marker unit consists of two distinct physical parts that can be firmly connected to each other but can also be easily released from each other. One part may be positioned close to the body and may therefore be for single use (cannot be disinfected) while the other part (can be disinfected and therefore reusable) attaches to the disposable part but has no direct attachment to the subject. The attachment between the two parts can be direct through fasteners, e.g., similar to ECG fasteners. Another alternative is that the two parts be connected through clothing or a blanket. For example, in one embodiment of the invention the disposable part is a patch that adheres to the body, while the reusable part consists of an active marker that is positioned on clothing and attaches to the disposable part through one or more fasteners. In the case of an active marker, the power unit may either be incorporated within the disposable patch or within the reusable marker.

The active markers can emit steady signals or coded signals. For example if the markers emit light, the intensity can be modulated according to a frequency that is predetermined and distinct for each marker location. In this way, each marker can be easily identified during operation. Furthermore, light patterns which can save on battery life can be employed for long-term monitoring.

3. Controller and Mount: The camera can be hung overlooking the subject on the wall, ceiling, a stand or part of the bed or any other fixture in the vicinity. A controller may be provided, which can be used to pan, rotate and zoom the camera's field of view freely in 3D either manually or automatically based on the video content. In addition to the camera positioning, it can be possible to adjust other camera features automatically based on the video content. Examples of such features are: focal distance, illumination level, white balance and optical filters. Providing such controlling elements is well known in the art and is not therefore described herein, for the sake of brevity.

Many different embodiments of the invention can be provided, comprising different elements, such as sensors, software for calibration or other purposes, etc. Some such elements are described below, it being understood that invention is not limited to embodiments using such elements, and that many other additional functional elements can be added, which are not described in detail hereinafter since they will be understood by the skilled person.

Additional Sensors

The camera visual sensor may also be equipped with a depth sensor providing the distance of each monitored pixel from the camera.

Video Detection and Tracking

Figure 2:
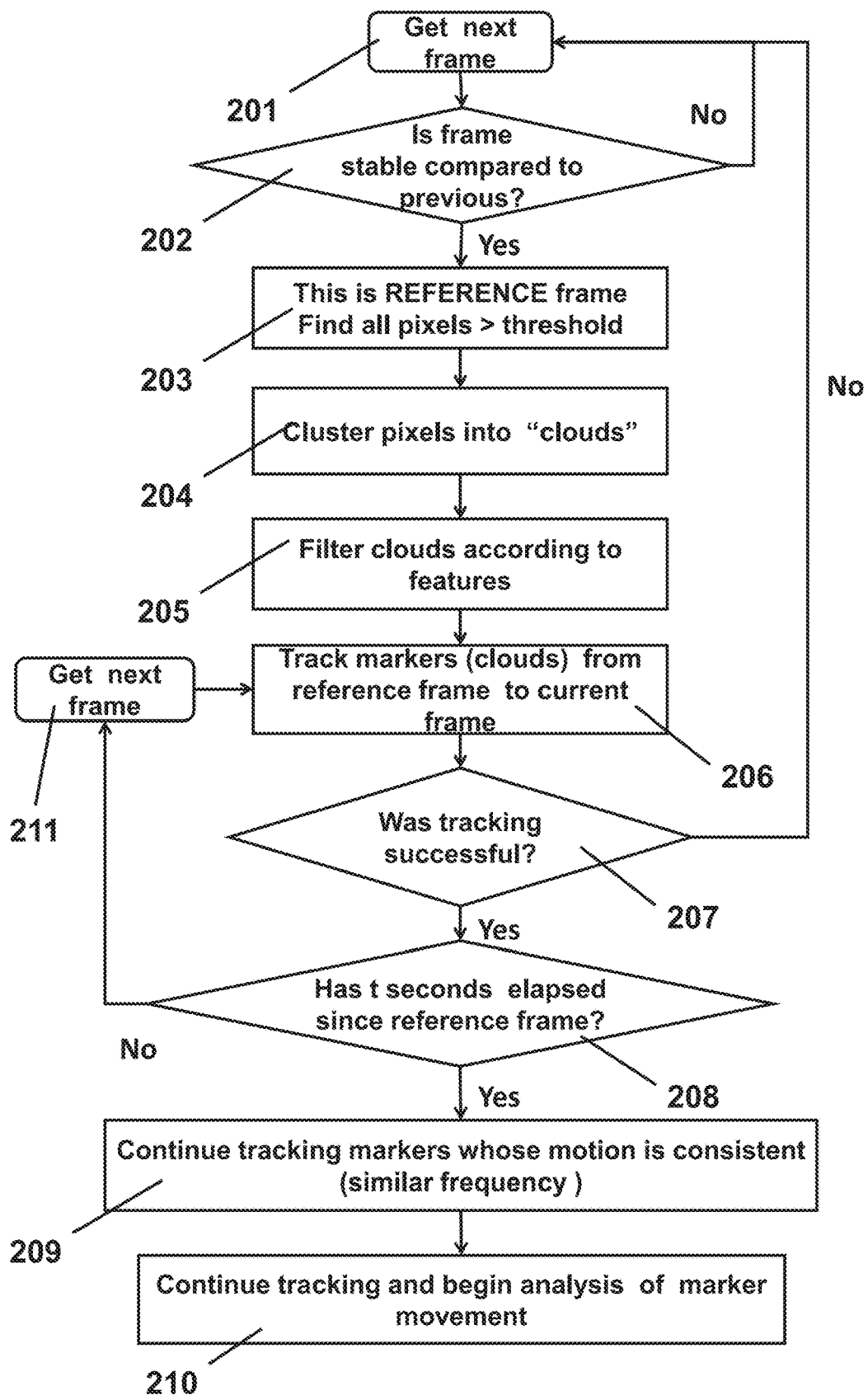
FIG. 2 is a flow chart of a detection stage, according to one embodiment of the invention.
Figure 3:
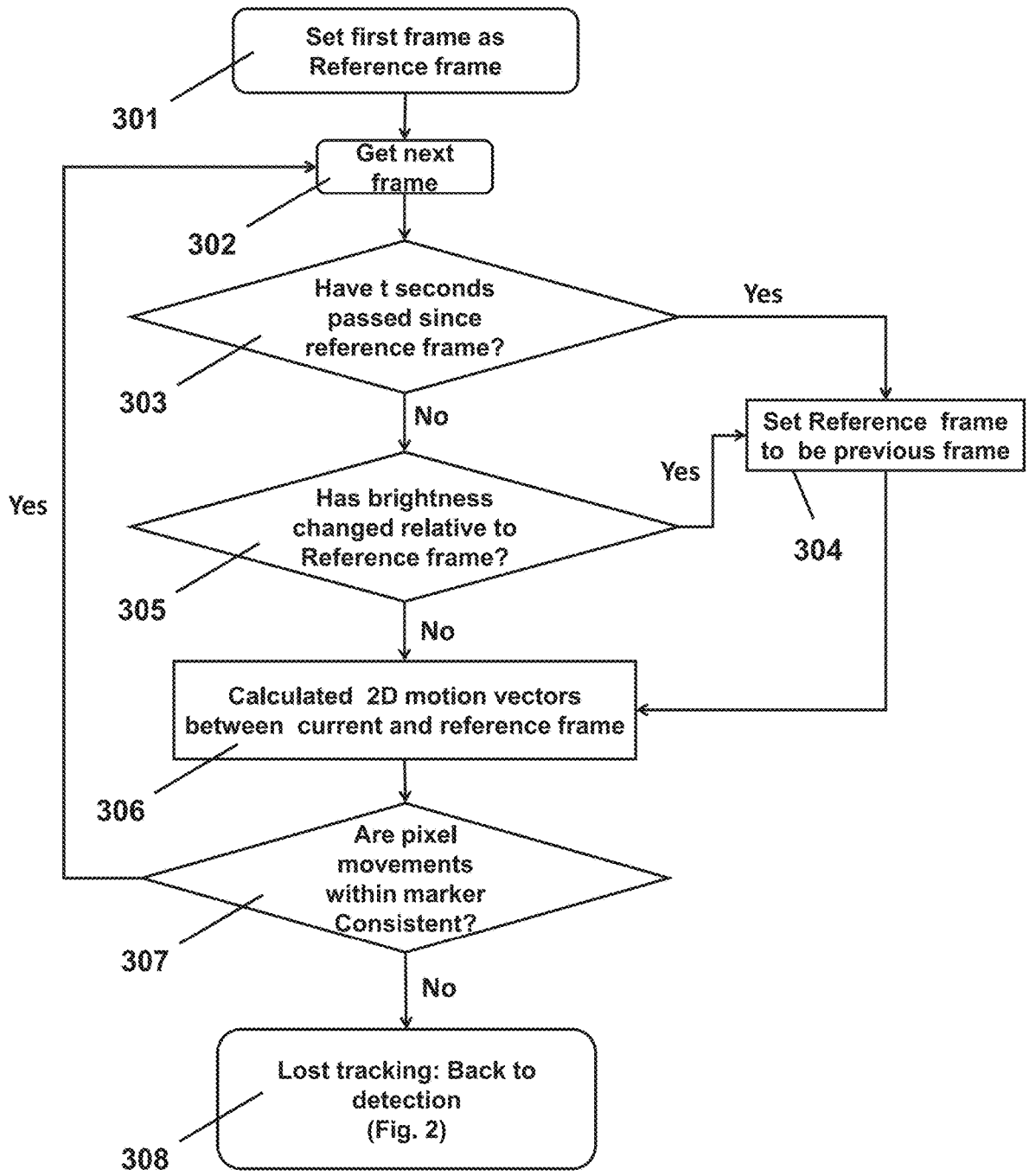
FIG. 3 is a flow chart of a tracking stage, according to one embodiment of the invention.

The following relates to the detection and tracking of the markers using 2D video images (FIGS. 2 and 3). Later on a description is provided how the depth information can be obtained from standard 2D images or from a 3D camera or stereo camera For the first video frame or any frame in which the markers from the relatively recent frames were not all tracked, an attempt to detect the markers is carried out. Detection on the intensity image (or sequence of images) can proceed in the following steps:

1. Pixels with high intensity are marked. This is done using a fixed threshold or one that adapts to the local noise according to the local intensity distribution. For example, all pixels whose intensity is higher than 5 standard deviations from the mean of the neighborhood intensity distribution.

2. The marked pixels are clustered to connected components using chain clustering for example. Two pixels belong to the same cluster if there is a path of marked pixels that connect them, each within distance d of each other.

3. The various clusters are the candidate markers. They are now filtered according to a priori known features of the markers such as their size, eccentricity, bounding box size, temporal frequency and gray levels. For circular markers, principal components values of the candidate clusters are useful features. Position of the candidate clusters relative to the bed or body silhouette can also be used to filter out spurious clusters.

In the case where the markers are "flashing" and do not appear in each frame, the above analysis is carried out for a series of frames where the extent and identity of the frames in the series depend on the flashing frequencies. The final candidate markers for step 3 above consist of the unified set of markers obtained from the frame series.

In the cases where the marker produces a variable shape and dispersed light pattern the clustering is carried out differently. This can occur for example in the presence of a blanket which may scatter the light reflected or emanating from the markers, dependent on the folds in the blanket and the relative configuration of the blanket relative to the markers. In these cases, chain clustering with a single threshold on the intensity image as described above may not be sufficient to identify a single marker consistently. A marker may be composed of several disjoint clusters which are the "seeds" of its more extended light pattern. In order to capture the marker signature, the seeds may be expanded by region growing techniques to unite the seeds to a single signature. This signature is saved as a set of pixels with their gray levels. In addition the presence of a specific temporal behavior for a particular marker is used to associate disjoint pixels to a common signature.

Once the clusters in a frame are detected, they are tracked over the following frames (as described below). If the tracking was not successful for all the detected markers, the detection is reinitialized on the new current frame. Successful tracking means that the positions of all the detected markers were determined in each frame, that the frame to frame displacement of each marker does not surpass a predefined threshold and that this displacement is consistent across the marker pixels and the individual emitters. The threshold is set using the maximal expected speed of the breathing motion. It can be later adjusted per patient during the baseline setting per patient described below.

In case the tracking was successful for a short time, say 3 seconds, the tracking is continued in time on the "valid" detected clusters. A valid cluster is one whose motion is consistent in terms of frequency of motion with the major detected markers (those in the trunk of the body). This can be analyzed by calculating the largest component of the Fourier Transform of the cluster displacements over say 10 seconds and removing clusters whose frequency is far from the median frequency of the chest & abdominal markers Once it is verified that markers in the field of view have been detected as described, one proceeds with tracking these markers in the coming frames. From time to time detection is carried out again to detect markers that were momentarily absent or had a low signal in the initial detection.

The tracking of the markers can proceed by calculating the optical flow patterns in order to identify the local motion within the image. The Lucas Kanade method can be utilized (B. D. Lucas and T. Kanade, *An iterative image registration technique with an application to stereo vision*. Proceedings of Imaging Understanding Workshop, 121-130, 1981).

The tracking is carried out relative to a reference frame in order to avoid accumulating frame-to-frame errors. The reference frame is updated from time to time due to the fact that the scene is changing over time. One possibility is to update the reference frame when one or more of a specific set of criteria are met. Examples of these criteria are:

Non-breathing movements are identified;
Illumination conditions of the scene have changed significantly (total intensity change of marker cluster relative to same marker in reference frame);
Every preset time period (e.g., 30 seconds)

In order to improve the sensitivity of marker detection, the tracking can be used as a filter as follows: the single frame detection method may be set to produce an abundance of objects some of which are not actual markers on the subject's body. Once they are tracked, criteria for filtering them can be used based on characteristics of their movement. For example, markers that remain static for a long time even when subject makes some position change can be filtered. Furthermore, if one is concerned with tracking only breathing motion, non-static markers with a different frequency of motion (or uncorrelated motion) than the identified breathing markers are filtered.

From Video to Respiration

For each marker that is detected or tracked in a frame, its center of mass image coordinates are calculated by averaging the locations of the pixels in its cluster. The raw data of positions is processed further in order to reduce noise due to the measurement systems and subject motion.

Noise Reduction

Each individual marker time series (2-dimensional x and y) is processed on-line using noise reduction filters, such as those using a measurement window around each point to process the data using a mathematical operation such as averaging, weighted averaging, or the median operation. Bandpass filters damping high frequency noise can also be applied. In addition, the a priori knowledge of the rigid geometric arrangement between the individual markers enables applying Kalman filtering to obtain their position at higher accuracy.

Another possibility of isolating breathing motion from other motions, such as body movement, heartbeat or body tremors, is to first learn the principal image direction of the breathing vector for each marker when the subject is at rest. All motion in the perpendicular direction is regarded as "noise" and removed. Other physiological information can be extracted from this removed "noisy component" such as the frequency of cardiac oscillations (heart rate) and tremor frequencies. Heart beats can be identified using band pass filters associated with frequencies learned based on subjects data or from an additional hear rate sensor (for example the pulse-oximeter).

In the case that the camera is mounted on a non-stationary devices such as a pole, a lamp arm or another moveable accessory, additional noise may enter the video. Such noise can be tracked by following the movement of a stationary object such as a wall or floor or a marker on a wall. Another way the movement can be tracked is by using a 3D actuator connected and recording camera vibrations and movements. These movements can be used to align camera frames. Camera vibrations can be compensated by removing the vibrational frequency from the markers path history in Fourier space.

Extracting Subject Position

In order to quantify measurements it is advantageous to know the subject position at any point in time. The available assigned positions may be for example, the following ones: Supine (belly-up), Prone (belly-down), On right side, On left side, Out of bed. The pose can be determined according to the inclination angle deduced from the one or more accelerometers. For example an abdominal marker will have an angle essentially parallel to gravity for the supine position, an angle of approximately 90 degrees for the lateral poses but with a difference in sign between left and right lateral. In another embodiment, the 3D position of each of the markers in the camera frame can be deduced, given the image coordinates of at least 3 emitters that are connected rigidly (see below).

The set of subject positions may be enlarged to incorporate intermediate positions, for example a left lateral pose with various degrees of bending of the spine. These poses can be differentiated for example by calculating the vector distance between an abdominal and chest emitter from reconstruction of the 3D locations in the camera frame. Chest and abdominal accelerometers can be used to determine their relative inclination to gravity; the addition of chest and abdominal gyroscopes to each marker assembly can provide the relative orientation of specific 1-d lines within each of the marker assemblies.

Extracting Non-Breathing Motion

The marker movements consist of respiratory movements, cardiac movements and other gross movements unrelated to the cardio-respiratory system. It is important for some applications such as sleep studies to identify periods of such movements, extract them, and continue measuring breathing parameters in their presence when possible. Such movements may include leg movements, twisting and turning in bed, bed-exit and others. The respiratory analysis may be carried out differently during periods of body movement and therefore these periods need to be identified.

As the markers are tracked one can identify frames in which there was significant non-breathing motion as follows: For each marker at each frame, the image positions of the marker in all the recent frames (say, 10 seconds) are analyzed through principal component analysis. When the body motion is pure breathing, the magnitude of the first principal component of each marker is significantly larger than the magnitude of the second principal component. The direction and absolute size of the first principal component vector is dependent on the marker location, relative camera position and subject's physiology. However, what is found to normal breathing motion is that locally it is along a fixed 3D axis throughout the entire cycle. By choosing a camera position and marker positions whose lines of sight are not parallel to these 3D physiological breathing directions, the local directionality translates to the 2D image. In the image coordinates, breathing motion is characterized by locally possessing a principal component that is significantly larger than the second one in the 2D image. Once the magnitude of the second principal component becomes significant relative to the first principal component for a few frames (for 0.5 seconds for example) of any chest/abdominal marker, it is an indication that some kind of significant non-breathing motion has occurred. At this stage tracking is reset and detection is carried out again. In cases where the camera line of sight is close to parallel with a marker breathing axis, the above Principal Component Analysis should be carried out in 3D (see below how the 3D vector is reconstructed).

Additional indicators of non-breathing motion can be extracted: for example by counting the number of pixels who have changed their gray level significantly (greater than a fixed threshold) from frame to frame of the video sequence. The number of pixels which obey this criterion during breathing can be determined from a baseline period, say, 30 seconds when the subject being monitored is not moving significantly (asides from breathing motion). Using the statistics during the baseline period, the threshold on the number of pixels that change significantly for identifying non-breathing motion is set. Once the single marker criterion described above or the overall frame to frame difference is identified, an epoch of non-breathing motion is found. The epoch ends once the markers are redetected and can be tracked for a short period without non-breathing being detected.

The inertial sensors can also be utilized to identify non-breathing motion epochs according to their signal features such as the magnitude of inclination changes and their derivatives. Features from the various sensor signals (optical and inertial) may be combined to learn a classifier that identifies epochs (say 10 second intervals) of non-breathing motion; the classifier is trained on a database of subjects a priori and run during monitoring to determine epochs in which breathing parameters cannot be extracted due to significant non-breathing motion.

2D to 3D Motion Tracking

The 3D displacements of the markers in the body frame of reference needs to be determined in order to calculate various parameters such as breathing volumes. With a 3D camera, the additional depth coordinate of each pixel is provided. However, these coordinates are in the camera frame and not relative to a body frame of reference. The following description illustrates how the 3D motion can be obtained using only the 2D image coordinates and a marker that consists of 2 or more LEDs.

One possible marker configuration includes 2 LEDs fixed to a rigid plate and separated from each other by a known distance, say 4 cm. The structure of the marker can be that of FIG. 6 with electronic circuitry and battery source that powers 2 LEDs. Each of the 2 LEDS are detected and tracked as described above. In order to calculate their 3D displacement and vector direction, consider two video frames in time: the end of an exhalation (beginning of inhalation) and the following end of inhalation. These frames can be found by calculating 1D curves of the marker displacement along the instantaneous principal component direction and subsequently analyzing these marker displacements curves for minima and maxima using standard 1D methods. The shape of the quadrilateral formed by the four 3D positions of the 2 LEDS (two at the beginning of inhalation and two at the end), is well-approximated by a parallelogram. This is due to the physiological characteristic that the breathing vectors are more or less fixed over small body surface regions (say 5×5 cm) of the abdomen or chest. One condition is not to locate the markers over points of discontinuity such as the ribcage-abdomen boundary. The base of the parallelogram has fixed length since it on a rigid marker but the length of its sides is unknown. First we describe how the length is determined assuming the parallelogram angle was known. For this task we use well-known camera pose estimation techniques, which are used to determine the 3D camera position of a rigid body given the image coordinates of at least 3 known points in the object coordinate system (see for example POSIT algorithm in Dementhon and Davis, International Journal of Computer Vision, Vol. 15, June 1995). The above described parallelogram can be regarded as a virtual "rigid body"—two of its vertices possess image coordinates obtained from the frame at the beginning of the inhale while the two other vertices are determined from the frame at the end of the inhale. In the object frame, the coordinates of the vertices relative to a vertex at the beginning of inhale are 1. (4,0,0)
2. (h cos θ, h sin θ, 0)
3. (4+h cos θ, h sin θ, 0)

where θ is known, but h is yet to be determined. Had h been known, the camera pose could be determined using standard methods. So a set of values for h are assumed, say in the range of 1-20 mm, and thus a set of corresponding camera poses are determined. The correct h is determined as the one which leads to minimal least square error between the measured image coordinates from the tracking and the coordinates determined from the corresponding camera pose. In a similar manner the angle θ can be varied in addition to h in order to determine the camera pose with least square error. Thus the angle can be determined without prior knowledge.

Figure 11:
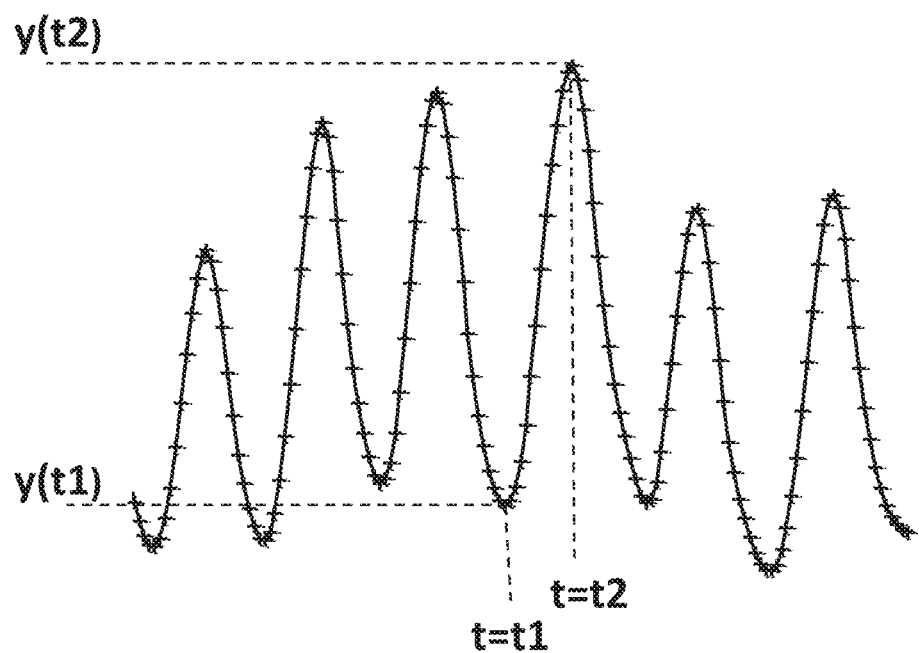
FIG. 11 is a breathing waveform showing a single marker's displacement over time.

Once the breathing vector from the beginning of inhale to the end of inhale is found, the displacements for intermediate frames can be found from the principal component displacement graphs by simple linear scaling. Specifically, for each monotonic segment of the 1D graph of FIG. 11, the following transformation is carried out from left to right:

$$y'(t)=y'(t1)+\text{factor}*(y(t)-y(t1))$$

where factor=Y3d(t1,t2)/(y(t2)−y(t1)). The function y(t) is the 1D original principal component projection at frame t, and y'(t) is the 3D displacement graph at frame t. A monotonic segment starts at frame t1 and finishes at frame t2. y'(t=1) is set to y(t=1) and Y3D(t1,t2) is the length of the 3d vector corresponding to h found for the breathing maneuver from frame t1 to frame t2.

In order to increase the accuracy of determination of the 3D displacements, markers with more than 2 LEDs can be used as follows:

1. In a first frame, say the beginning of inhale, the 3D camera position is determined using standard methods based on the knowledge of 3 or more points on the rigid body (the marker).
2. The positions of the LEDs in a subsequent video frame (end of inhale) are assumed to all be translated from their original positions at the beginning of inhale by a fixed 3D vector [a,b,c] that represents the breathing vector. Using the camera pose determined from the first frame (Rotation and Translation) along with the image positions of the LEDs in the second frame, the values of a, b and c can be determined by least squares.

In order to limit the power consumption or the use of multi-LED markers throughout the monitoring, the following methods can be used:

1. Prior knowledge learned by using 3 or more LEDs on a marker at specific body locations on a set of training subjects. For example, it was found that the breathing vector for an abdominal marker along the central superior inferior body axis is close to being perpendicular to the marker's rigid plane.
2. Learning breathing angles on a training set of subjects using multi-LED markers and applying the learned results to real-time monitoring of subjects using 2-LED markers. These learned angles are determined for a number of subject breathing patterns and a number of marker placements on the training subjects. The relevant vector directions according to body type (to be described hereinafter), anatomical location, body positioning and breathing type (deep or shallow for example) can be used once a test subject is monitored. Alternatively, a representative vector direction for a wide-range of conditions (approximate surface region, all breath types, etc.) is often sufficient.
3. Use 3 or more LEDs on each marker on subject in question during baseline setup or intermittently. These can be the same markers that are used during monitoring; in order to limit power consumption the extra LEDs are turned off during regular monitoring or flash in some time dependent way to reduce power consumption. During the baseline setup all the marker LEDs are used to determine the vector directions; subsequently only 2 or more of them are used to determine the vector displacement.

Another configuration in which 3D motions can be reconstructed is by using several distinct markers. For example, several single marker LEDs can be distributed at 2 or more distinct locations on the chest and the distances between them measured using measuring tape or some other measurement means at a particular time in the respiratory cycle (say end of exhale). From these measurements, the camera position can be determined. Using the directions of breathing motion at each of these locations (determined using methods such as those described herein), the breathing displacements can be estimated analogously to the way described for the multi-led markers using image frames at two different times (t1 & t2) in a single respiratory cycle, say beginning of inhale and end of inhale. Here the "virtual rigid body" that is being tracked is the 3D slab formed by the vertices of the marker locations at t1 (define one face of slab) and the marker locations at t2 (define second face of slab). In the specific case where there are only 2 single markers, the virtual slab reduces to a quadrilateral with two long almost parallel sides of known length.

Sensor Data Fusion:

The video analysis and inertial sensor measurements of breathing motion can be combined to provide improved estimates of the respiratory motion.

The video analysis of the marker motion essentially provides the respiration displacements of each breath in 3D space (length and direction). The accelerometer analysis provides a complementary independent view: in that it provides information regarding the curvature of the essentially 1-D breathing translational movements Combining the signals to calculate respiratory parameters enables more accurate estimation of respiratory parameters by combining independent aspects of the respiratory motion.

Furthermore, the markers and the accelerometer must be on the same rigid base or very close to each other, so that they actually measure the same body movement.

Missing Data:

Asides from achieving more accurate results by fusing measurements from both the imaging and the inertial sensor, the two sensors can be used to fill in measurements when one of the sensors cannot make a measurement, when there is no line of sight between the imaging sensor and the LEDs, or when there if a partial obstruction of some of the LEDs. This can be achieved by using the previously described Kalman filter with measurement covariances, which are dynamically changed according to the quality of the data measurements. For example, when a LED becomes completely obstructed, the covariance of its measurements is set to the maximal value for the filter iterations.

Physiological Measurements

Extracting Breathing Measures

Accepted clinical measurements such as respiratory rate, tidal volume, minute ventilation and apnea indicators can be derived from the sensing system. In order to obtain absolute estimates of some of these properties (typically for diagnostic purposes), calibration is needed between the measured signals and the respiration property. These calibration functions can be learned a priori based on subject attributes such as body shape, silhouette, weight, age, sex, BMI, chest circumference, and body position and data from a validated device for measuring air flow such as a spirometer. The calibration can also be updated using data from a phantom or a simulator. Note that calibration functions used should be taken with the subject pose and marker location taken into account.

Often for monitoring, the absolute value is not necessary but changes from baseline properties need to be quantified. In such cases, the calibration need not be carried out. In the following, methods for extracting a number of respiratory properties from the sensed marker signals are outlined:

1. Respiratory Rate: The respiratory rate is extracted by first extracting the dominant frequency from each available signal separately and then fusing these estimates together, say by averaging; For a video sensor, the signals analyzed are the 1-d displacements of the markers along the principal component axis in the last say 30 seconds; for an accelerometer/gyroscope the signals are the inclination angles to gravity. Periods of identified non-breathing motion are not included in the analysis window.

One method to extract the dominant frequency from the marker's cleaned (filtered, cleaned of noise and after non-breathing motion removal) signal, is through analysis of time series windows which include several breaths. For instance, this can be achieved by calculating the Fourier transform over a moving window of, e.g., ~20 sec every 1 sec. A Hamming window (Enochson, Loren D.; Otnes, Robert K. (1968). *Programming and Analysis for Digital Time Series Data*. U.S. Dept. of Defense, Shock and Vibration Info. Center. p. 142.) is used to reduce artifacts. The instantaneous frequency of each signal is taken to be the frequency with the largest Fourier component amplitude. Another way of calculating the individual respiration rates are in the time domain as the time difference between consecutive significant peaks or troughs.

The estimate of the actual respiratory rate is taken as a weighted average of the dominant frequencies found from each valid marker signal. The weighting can be taken proportional to the signal to noise ratio of each of the comprising signals.

2. Apnea and Hypo-apnea Events: These are events for which the subject has stopped breathing or has a very low breathing rate for over 20 seconds.

Apnea can appear with chest wall movements present as in an obstruction and there a more careful analysis is needed. First the amplitude of the chest movements is examined and if it is significantly lower than recent breaths it is suspected as an event. Furthermore, the phase difference between abdominal and thoracic markers is followed to determine whether a significant change 1 time may be obtained by obtaining the phase delay between two short time segments (10 sec for example) of the marker movements. For example, this can be achieved by taking the Fourier Transform of each segment separately and obtaining the phase difference between the relevant complex Fourier component of each of the two markers. The relevant component is the one that correspond to the extracted respiratory rate. Another method to find the phase difference between two markers is to average the time lag between their peaks and express it as a fraction of the cycle time; 50%, for example, corresponds to a 180° phase lag.

Periods of disordered breathing including apnea events can be found by building a classifier on signal windows (say 10 seconds) from all available sensors (inertial and image sensors). Relevant features are based on the amplitudes, cycle lengths and phase lags of the signals within a window. This classifier is learned on collected data of subjects with labeled apnea events. Such events are identified by a physician with the aid of a capnograph that continuously measures the concentration of $CO_2$ in exhaled air (Lifesense, Nonin Inc.). This classier can be combine with the classifier for non-breathing motion epochs described above.

3. Inhale time, Exhale time: For each marker displacement trace, the time evolved between a peak and the following trough can be used as a measure of the inhale or exhale time, depending on the marker location.

4. Breathing Variability: Breathing variability can be calculated as the entropy of the lengths of the breathing cycle. It is often an indicator of respiratory distress.

Figure 14:
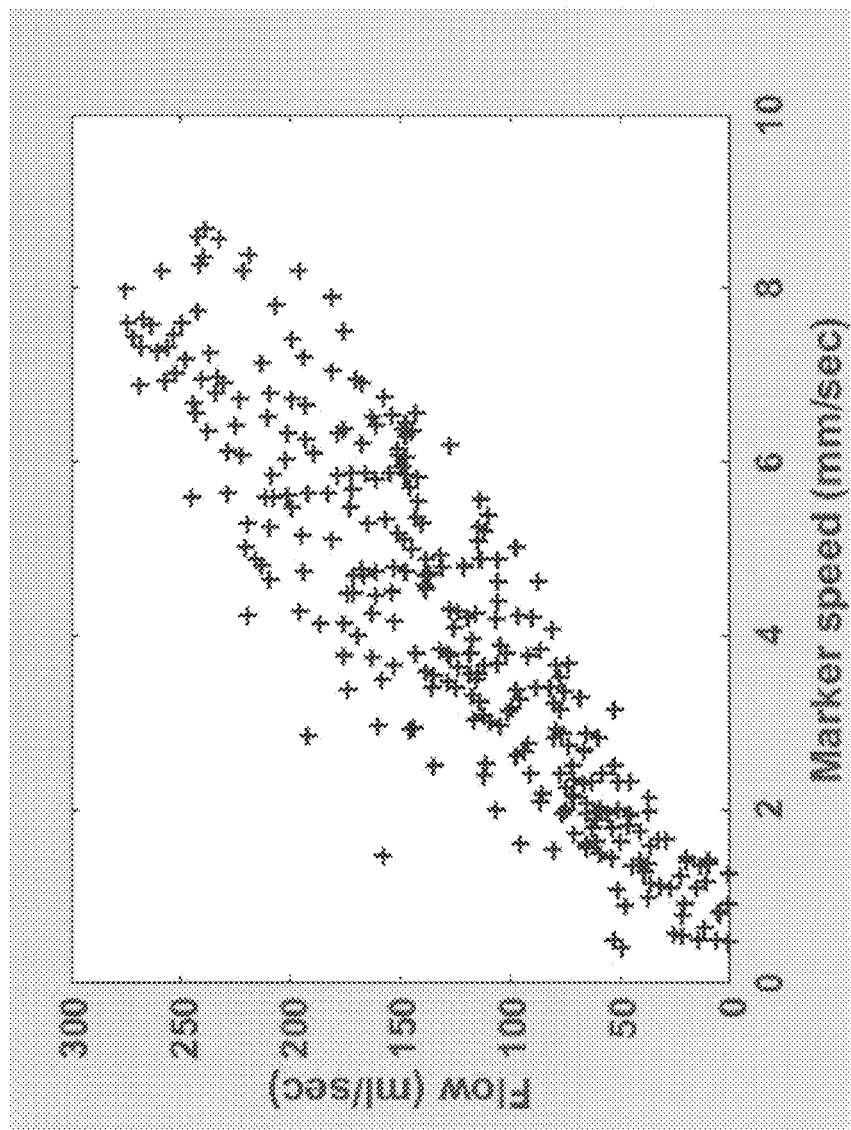
FIG. 14 is a scatter plot depicting spirometer flow readings versus the speed of a single marker placed on a subject.

5. Tidal Volume: One embodiment for calculating tidal volume (the amount of air displaced or inhaled per breath) proceeds through calibration of the subject with a spirometer for a few breaths. A model is learned for the dependence of the spirometer flow versus a marker's "flow", which is essentially the derivative of its 3D displacement function during a breath, smoothed if needed. Flow data from the inhale phase of several breaths of a subject who has breathed through a spirometer is shown in FIG. 14. The flow readings of the spirometer are shown versus the speed of a single marker's displacement. A model, for example a one-dimensional linear one, can be fit to this data and used in runtime to estimate the flow during each breath. A more detailed mode is also possible. According to another example a model with an additional parameter representing the scaled time within the breath may be used. Alternatively, separate one-dimensional models can be learned for each phase of the breath such as: beginning of inhale, midst of inhale and end of inhale.

Prior to fitting the spirometer mouth flow to the marker signals they need to be aligned, say by aligning the time of the maximal displacement to the end of inhale. Standard integration of the flow during one breath provides an estimate of the tidal volume based on inhale. A similar model can be learned to estimate the exhale phase. The inertial sensors can also be used to build a model based on their velocity profile which can be obtained from integration of their acceleration profile in the global frame (with gravity removed from the acceleration profile as described above). In the presence of more than one marker or inertial measuring unit, the tidal volume is estimated by a weighted average of the individual model estimates, with weighting provided by their overall reliability measured by their goodness of fit at calibration.

The learned linear models are sensitive to several parameters such as the anatomical position of the markers and the specific subject pose. The subject pose can change during the monitoring (during sleep, for example). Non-rigid changes of subject's thorax pose can be identified by tracking in real-time the relative 3D pose of one marker relative to the other marker using well-known 3D reconstruction methods, such as described above. In cases where a significant change in relative pose of the 2 markers is identified, the calibration model used is modified. The calibration model to be used in runtime is modified according to the model learned at calibration for the specific subject's pose. Specifically, for the linear model it was found that small changes in pose (say from supine) can be modeled by adding a linear term in the difference in "bending" angle from the original pose. This "bending" angle can be taken as the angle between the planes of the chest and abdominal markers. The coefficient of this linear term is learned by varying the subject position during the calibration procedure. This coefficient can be obtained either from the image sensor measurements with 3D reconstructions or from the kinematic sensors' inclination estimation as described above. In the case of the presence of a single marker, absolute pose changes can be identified and calibrated for a priori (using a similar calibration procedure).

In a similar manner, small anatomical position changes in the marker location require a modification of the linear coefficient of the model which is learned at calibration. Changes in marker position relative to anatomy typically arise when the marker is not adhered to the subject's body, but rather is attached to a strap or vest worn by the subject. Changes in the anatomical marker position are carried out by tracking the 3D position of the marker relative to anatomical landmarks on a subject. There are several possible embodiments: in one embodiment, a fiducial marker can be placed on an exposed part of the body, such as on the neck; this marker may be reflective and tracked only intermittently when movement of the main markers is suspected. Changes in the relative 3D location between the fiducial and main markers can be used as an indication of marker movement. In cases where the marker movement exceeds a predetermined threshold, an alert may be issued to call the staff to adjust the location. In cases where the movement is smaller, the model's linear coefficient can be adjusted according to what was found during calibration. In another embodiment, anatomical lines such as the midsternum anatomical line can be tracked in the image using deformable registration methods on the body silhouette which, can be found as outlined below.

In another embodiment, the relative 3D movement between the rigid chest and abdominal markers can be decomposed into 2 components—the first resulting from a body "bending" component and the second consisting of other marker motions. The resulting magnitude of the relative 3D movement between the markers (due to the second component) can be used as an indicator of the magnitude of the markers movements relative to the subject's body (which cannot be explained solely by "bending"). The relative 3D movement between markers can then be decomposed into these 2 components to determine the amount of markers movements relative to the subject body. In order to determine which of the 2 markers has moved, the distances to the body silhouette or facial features can be evaluated, to determine which one is more consistent with previous measurements during monitoring.

For carrying out the linear calibration the tidal volume can be used as opposed to the actual flow measurements. In this case, the flow measurements are reconstructed by multiplying the relevant marker speed by the ratio of tidal volume to maximum displacement for the breath in question.

In other embodiments, the calibration of each subject with a spirometer on a few breaths can be replaced by calibration from a previously acquired database of subjects as described below.

Another method for calculating the tidal volume is through modeling the abdominal and thoracic cavity shape. For example the shape can be assumed to be a double cylinder. Both cylinder walls expand during inhalation and contract during exhalation. The heights of the two cylinders change with breathing due to the movement of the diaphragm. The thoracic cylinder and abdominal cylinder have different mean radii which can be approximated from the image by using edge detection on the image to find the body edges, at one or more body positions. The known physical marker size can be used to convert these measurements to physical units. During runtime, the marker displacements and the angle of the camera are used to calculate tidal volumes through the model.

Yet another modeling technique can utilize the 3D modeling of the thorax as described herein above. The extracted marker motion can be superimposed on the 3D model to extract the volume change during exhalation.

6. Minute Ventilation: Integrate tidal volume over one minute.

Extracting Non-Breathing Measures

There are other measures of motion that can be found from the monitoring system that are not associated with breathing, but can give information on sleep quality and behavior that can be extracted from the marker movements. Some of these are:

1. Leg Movements: By tracking markers on legs or other extremities the extent and number of these movements can be calculated. Such movements are associated with the diagnosis of restless leg syndrome.

2. Eye Movements: Eyes, when open can be detected from the video imaging without the necessity of markers. In order to classify eye movements during sleep, small kinematic markers (including strain sensors) placed on or above the eyelids or by the corner of the eye, such as by means of a sticker and wireless transmission, can be used. These small kinematic markers may be used for sleep staging for quantifying eyelid movement to associate a specific eyelid movement pattern with a corresponding sleep stage or for quantifying the continuity of sleep (eye openings). It will be appreciated that these kinematic markers may be used for sleep assessment during anesthetic procedures.

3. Posture stability: The number of position changes during sleep can be tracked easily due to the markers that move in and out of the field of view. The actual body position at each time of sleep can be found and alarms can be set to caregiver if person needs to have position changed (subjects with bedsores, infants who are not to be positioned in prone positions, etc.).

4. Bed Exits: The number of bed exits and bed entries can be detected and alarms setoff in real time if person does not return to bed or falls near bed for example.

5. Heart Rate: The heart rate can be obtained from markers located near to chest. This can be best done by finding peaks in the Fourier transform of the displacement signal of each marker in the range of, e.g., 40-140 bpm for adults.

6. Tremors/seizures: Continuous trackable motion in all the markers as well as motion in a large fraction of pixels found within the body silhouette indicate a tremor.

7. Eye micro-tremor: The characteristics of eye micro movements are related to the level of sedation. The described sensor can be used in conjunction with a marker to track these movements as follows: A marker can be adhered to the eyelid or around the eye, such as a strain sensor, a thin retro-reflective adhesive sticker or else IR reflective polish can be applied to eyelids or eyelashes. An alternative is to attach the marker to the side of the face near the eye and have a thin flexible object connecting it to the eyelid. It is possible to track movements by detecting and tracking the boundaries between eyelashes and eyelids in the image. Since the movements are of high frequency (~80 hz) and of small amplitude (up to several microns). The choice of camera sensor should be made accordingly and also the placement should be closer to narrow the field of view. One possibility is to attach the camera to an eyeglass frame rather than to the bed.

In order to cancel camera jitter movement and head movements, other reference points away from the eye are also tracked such as markers on the cheek, forehead or earlobe. These signals are analyzed to detect the main frequencies of motion which can subsequently be removed from the eyelid signal. The resulting signal can be further analyzed to determine the frequency of the micro eye tremors.

The eye-tremor and breathing monitors can be configured to use the same sensor or distinct sensors.

8. Head Movements: Often there are head movements arising from an obstruction and manifesting itself as snoring and increase respiratory effort.

Respiration Quality Measures and Warnings

Respiration is monitored in order for an early warning alert to be issued if a problem is about to occur. The system produces an online early warning alert based on personalized per subject data and based on recent continuous measurements.

The ubiquitous problem with alert systems is that they are often unreliable and therefore lead to alarm fatigue, in which alarms are often ignored. We describe a system which provides a more reliable early warning, is more immune to artifacts and classifies the overall respiratory information sensed. In addition, a quality measure is provided, which quantifies the reliability of the current measurement. The early warning system is based on a multi-dimensional analysis of the respiratory waveforms and personalized to the current attributes of the subject being monitored. This should be contrasted to typical monitoring systems that track a single feature, for example the respiratory rate. In such systems, an alarm will typically be set off whenever the derived respiration rate declines or exceeds fixed preset minimal and maximal thresholds. The approach that introduce here is different in that it is adaptive to the subject but reliable in that it is based on a large amount of data. First, features from the subject are used (age, sex, thoracic size, etc.) and then various feature are extracted from the recent measurements. These can be the outputs from the video imaging system described above or from other devices or from a combination of several devices. For example, the raw signals may include those from an end tidal $CO_2$ capnograph, a pulse-oximeter and the video system described above with a single marker. The measurements can be impedance measurement made through leads attached to a subject. The identity of the features, mathematical quantities derived from the measurements time series, are determined in the training stage described below. A classifier is trained in this feature space during the training stage which is performed either in advance or online. The classifier can be a two-class one that differentiates between normal subject behavior and abnormal behavior. Using the classifier, a score is assigned continuously based upon the measurement data, with 1 indicating typical baseline behavior while a lower score, e.g., 0.5, represents the edge of normal behavior below which outlier behavior is observed. In addition to this "functional score" that is calculated based on training data, a quality score is calculated denoting how reliable the basic measurements are in cases where this is possible.

Signal Features

The features are calculated from the various signals on various timescales and typically depend on the physiological source of the signal. For example, the respiratory rate calculated from a 20 second time series signal of several of the video markers described above can be one of the features. Other features can quantify the trend of physiological quantities, such as the derivative (trend) of the respiratory rate over consecutive overlapping 20 second intervals. Similarly, average amplitudes of the respiratory signal peaks and troughs over 20 second intervals and their derivative over time can be used. The initial set of features can be reduced further in the training stage to reduce over-fitting of the classifier using standard methods.

Training

A classifier is trained using training data, which consists of training vectors that consist of the set of features and the label of one of the classes to be classified. The label may be "normal", "coughing", "sensor disconnected", "risky", and so forth. If sufficient data exists for more than one-class of behavior, a multi-class classifier map be trained. Minority classes with few data points can be grouped to a larger class labeled "artifacts" for example. In the case where labeled data does not exist or predominantly belongs to a single class, a single class classifier can be trained. Frameworks for learning such classifiers exist, for example the SVM one-class classifier (B. Scholkopf et. al., Estimating the support of a high-dimensional distribution. Neural Computation, 13(7), 2001).

Standard feature selection methods can be used to reduce the dimensionality of the classifier problem, such as PCA, and methods that rank the features according to their discrimination ability. The forgoing applies in general to training a classifier based on a fixed training set that is collected a priori to monitoring. However, if the data is collected a priori, it may not be relevant to the baseline characteristics of the subject in question, thus leading to an inaccurate classifier. An alternative would be to train the classifier based on the initial period of monitoring the subject, e.g., the first few minutes when the medical staff is in the vicinity. However, this greatly limits the amount of training data that can be used and thus can severely limit the generalizability of the classifier due to over-fitting. Again the classifier results may not be reliable. Our proposed methods involve forming training sets which are relevant to the subject in question and enable the incorporation of a large amount of data. Several variants which can be used alone or integrated together of forming a training set are outlined below:

1. Augmenting training sets online: The data from a monitored subject can be added to the database by adding it as time segments of e.g., 10 minutes with all its features. In addition, the periods of respiratory depression can be labeled according to preset conditions such as respiratory rate <8 or minute volume <3 liter. Using such a criterion, all the data can be labeled according to how long they precede a respiratory event. This data can be used in future training sets of the classifier since it can be labeled as "normal" and "risky" depending on how long before a respiratory event they were extracted.

2. Subject training set selection "on the fly": One method is to train a classifier based on data from a subset of the total available subjects. This subset is chosen so that it is "closest" to the subject in question. One method this can be done is by carrying out a clustering procedure (e.g., mean-shift clustering) in the feature space composed of the data from all the subjects, including the initial data of the subject in question. The subjects, whose data falls mainly in the same cluster as those of the subject are those used as the training set. In order to improve stability yet further the clustering can be carried out many times with different parameter values; the number of times each subject falls in the same cluster as the current subject is recorded.

Subjects that fall in a majority of the experiments in the same cluster as the subject in question are used for the classifiers training set.

3. Training set selection "a priori": The data from all subjects can be a priori clustered as in method 1 to obtain subsets of subjects with similar physiological signal features. More than one clustering experiment can be used to produce additional subsets that may intersect previous clusters. Each such cluster is a candidate training set and the one that is chosen is the one who is closest to the current subject. This subset can be chosen according to the distance of the cluster's center of mass to the current subject's features mean value. In addition, differences in the principal component directions in feature space can be incorporated into the distance matrix between the two distributions.

Another method of finding the distance between the current subject and the subsets is to determine the overlap volume between each cluster distribution and the current subject distribution. Each such distribution can be approximated by an ellipsoid using the covariance matrix and the center of mass in feature space. Additional criteria than can be taken into account in calculating the closeness are subject attributes such as age, medical status, sex and base vital signs.

4. Transforming training set: Another option of utilizing the original training set for the new subject is to scale the individual subjects to normalized coordinates. For example, a feature value $f_i$ can be transformed as follows:

$$f_i' = \frac{f_i - \mu_i^{(p)}}{\sigma_i^{(p)}} \quad (4)$$

where $(\mu_i^{(p)})$, $(\sigma_i^{(p)})$ are the mean and standard deviations of the feature i for subject p. After transformation the classifier can be learned on the transformed data set.

5. Selecting time segments for training set: Using the labeling of time segments as described in #1 above the relevant time segments from the subjects who were chosen to be included in training set are used.

The output of the training stage are mathematical formulae whose input are feature vectors and whose output is a class probability—the probability that the feature belongs to a specific class of the classifier. In addition, regions of the feature space that are associated with non-normal respiration patterns are assigned informative clinical descriptions: such as "Apnea", "Shallow Breathing", etc. These regions and abnormalities are assigned a priori based on pre-assigned rules (based on expert rules).

Runtime

In runtime, an initial class is assigned continuously based on the class with the highest score of the learned functions. In cases where a global normalization is applied to the raw features, the normalization factor is updated during runtime on the previous data of the subject in question. There are many adjustments that can be made in order to improve reliability of the monitoring such as:

1. In cases where the class association is not clear-cut an "undecided" tag can be associated with this time.

2. A quality measure is associated continuously in time. For the video sensor, whenever non-respiratory body motion is identified, the quality score is reduced from 1. The amount that it is reduced depends on the prediction error of the motion, the larger the error the more it is reduced (the minimal quality measure is 0). Also if periods of coughing or talking are identified using other sensors (for example acoustic sensors), the quality measure is also reduced. Any indication of artifacts in one of the sensor signals should be used to reduce the quality measure of the other sensor signals.

3. Due to missing measurements (subject out of bed), it may not be possible to calculate the classification at specific times. The class assigned at these times can be tagged as "unknown".

When the classier output is not "normal", the suspected anomaly can be output based on the feature values and predetermined rules. Examples of such rules are:

1) High respiration rate (28 breaths/sec) with low variability (0.2);

2) Hypoventilation: Breathing effort is low (Amplitude 50% of normal) and respiration rate is low (5 breaths/min);

3) Obstruction: Paradoxical breathing.

Output: Alarms and Communication

Typically, a class output that is neither "normal" nor "unknown" can trigger an alarm or warning to be issued. In order to increase reliability, a delay time (e.g., 10 seconds) may be applied before an alarm is issued. If during this delay time, the measurements return to the "normal" class, the triggered alarm will not be issued. Alarms can be audible with sound associated with severity and type of breathing pattern. They can be communicated to a variety of output devices either by a wired or wireless connection, such as to a bedside monitor, a handheld monitor, a mobile unit or a central nursing station.

Calibrations & Baselines:

Camera Calibration:

For accurate reconstruction of 3D marker and subject coordinates, it may be necessary to calibrate the camera once first connected using known grid pattern targets (without a subject). In some embodiments the camera is used at two positions to mimic stereo acquisition. Here too the camera should be calibrated with respect to the fixed known physical baseline (for instance, a rod placed on the bed). These calibrations can be achieved by many available tools (see for example: http://www.vision.caltech.edu/bouguetj/calib_doc/htmls/example 5.html).

Spirometer-Based Calibration Per Subject:

The normal baseline tidal volume for an individual depends on many factors such as: age, sex, obesity, pose, disease conditions, time evolved since anesthesia, etc. One possibility for calibration of baseline tidal volume of a subject is to carry out a calibration procedure of the above video device versus a spirometer which measures continuous pulmonary flow rate of air inhaled and exhaled. In order to verify how the markers move at different tidal volumes and in different poses, additional calibration measurements are needed to be carried out on the subject. These tests can be done prior to surgery or to an invasive or imaging procedure, for patients who are to be monitored during or post procedure/surgery.

Limited Spirometer Based Training Set Followed by Personalization:

An alternative to the calibration per subject is to learn/build a model on several subjects or subject simulators a priori in a training session in which several breathing patterns and poses are recorded both with the video device and a spirometer. In addition, other physiological data may be collected on these training subjects using movement sensors such as an image sensor, kinematic sensors, specific covering (for example a snug sheet or undergarments only) and possibly additional markers. In particular the following information can be collected:

1. Silhouette of the trunk area which moves during breathing: This is achieved in a number of ways but most simply by looking at differences of video frames taken at opposite phase during a respiratory cycle when the scene is illuminated. Pixels which change significantly more than they do for consecutive frames participate in respiration. These pixels can be pot processed to form a smooth region by region growing techniques.

2. 3D shape of subjects trunk using either a large number of markers as described above or using shape from shading techniques with specific ambient illumination (B. Horn. Obtaining shape from shading information. In P. Winston, editor, The Psychology of Computer Vision. McGraw-Hill, New York, 1975). Other methods of determining 3D shapes of human bodies can be used (see for example: B. Allen, Learning body shape models from real-world data, PhD Thesis, University of Washington, 2005). These are based on using a 3D camera in the training set from which the 3D body shape can be extracted. Furthermore the dominant features that differentiate between body shapes can be identified and mapped onto features that can be deduced from a regular 2D camera. For a test subject, these 2D features can be collected in a calibration session and mapped to find the relevant 3D body shape.

3. Various distances between body landmark features and/or markers and/or features of covering.

For each subject the spirometer flow rates are fit to a function of the marker motion signals. The number of data points entering the fit is according to the sensor and spirometer sampling rate, which is of the order of tens of samples per second, so that say a 5 minute trial involves several thousand data points. This is repeated for additional subject poses (lying on the side, for example). The volume function can be the result of a non-linear regression scheme, e.g. SVM regression (B. Sch¨olkopf and A. J. Smola. *Learning with Kernels*. MIT Press, 2002).

This model is kept in a database that can be accessed by the computer device of the breathing monitor. The model learned can be a linear function of the displacements; the phases can be taken into account by using signed displacements which are determined by setting a reference zero displacement for each marker. One way the zero is assigned is by computing a moving average of the raw displacements over the last few respiratory cycles (say 5 breaths for example). The signed displacement is obtained by subtraction of the reference zero displacement from the measured one at each time point. The relative weights between markers can be based on their relative "reliability" which is provided by the variance in equi-volume measurements or the variance of displacements during stable tidal breathing.

Alternatively, the phases can be taken into account by learning different models for different scenarios of phase relations between the markers. For example one function for all markers in-phase, another one for chest and abdominal markers out of phase, and so forth. Once a new subject is to be monitored, a short automatic calibration session (e.g., 30 seconds) is performed according to a predefined protocol such as "subject lies on back" is undertaken at which time various relevant measurements are made for an estimate of the subject's silhouette and 3D shape as in the training set. In addition other features related to trunk size are measured: These could be the distances between markers for example which can be extracted using the device's image frames or distances between body landmarks identified through image analysis or manually. In addition, physiological features are recorded for new and database subjects such as age, sex, height and weight.

Using the data gathered on the current test subject, the "nearest-neighbor" database subjects are extracted from the database. The distance between two subjects is measured for instance by measuring the distance between their trunk images (within silhouette) as follow:

1. The two images are registered using body landmarks and markers locations placed in corresponding anatomical positions. The registration is non-rigid but can be confined, for instance, to Affine transformations.

2. The distance between 2 images is determined by their scale factors (for example by the difference of the geometric mean of the scale factors to 1).

Once the relevant data base subjects that match the current subject the closest are found, the dependence of spirometer pulmonary flow readings on marker velocities found for the database subject is utilized to estimate volume as described herein.

Change of position: The marker movements and breathing volumes change as a function of subject pose. The pose of a subject is deduced in real time as described herein. For each subject position, the relevant database estimation for the volume is used. However, the relevant "nearest neighbors" from the database are selected during the initial auto-calibration session of the test subject.

FIG. 1 is a flow chart of the monitoring step that starts with the inputs of the first few frames 101 after which, in step 102, the markers are detected according to the procedure of FIG. 2. The detection step is followed by the impact of the next frame 103 after which, step 104 the markers are tracked over time as detailed in FIG. 3. From the frames the subject's pose is extracted in step 105, and the respiration properties are calculated in step 106, as further detail in FIG. 4. At the end of the calculation process the system checks, 107, if the tracking has been lost and in the affirmative case the process is started anew in step 101, while in the negative case the next frame is input in step 103.

FIG. 2 details the detection steps. At the beginning of this step the system already has at least one frame and the detection starts by getting the new frame, 201. A comparison step 202 is performed to determine whether the frame is stable compared to the previous one. In the negative case another frame is obtained and the process starts again at step 201, while in the affirmative case the frame is set as a reference frame and in step 203 all pixels greater than a threshold value are located. The pixels are then clustered into "clouds" in step 204 and the clouds are filtered according to their features in step 205. In step 206 the markers (clouds) are tracked from the reference frame to the current frame and the success of this tracking is verified in step 207. If the tracking was unsuccessful the process starts again at step 201, while if it was successful after t seconds have elapsed since the reference frame (verified in step 208) tracking of markers whose motion is consistent (similar frequency) is continued in step 209, and the analysis of marker movement begins in step 210. If the time that passed is less than t seconds, the next frame is obtained in step 211 and the markers are checked again in step 206.

FIG. 3 is a flowchart of the tracking procedure, which starts by setting the first frame is a reference frame at 301. Then, the next frame is obtained, 302 after which the system checks, in step 303, whether t seconds have passed since the reference frame, in which case the last frame is set to be the reference frame in step 304. In the negative case, step 305 checks whether the brightness has changed relative to the reference frame, in which case, again, the frame is set to be the reference frame in step 304. In the negative case, the 2-D motion vectors are calculated between the current and the reference frame in step 306. This also happens after the last frame has been set to be the reference frame in step 304. The system then checks whether the tracking is successful using criteria such as making sure the extent of the marker movement is not too large, that the pixel movements within the marker are consistent, and that the mean square error in the numerical fit is not too large in step 307, and in the affirmative case it goes back to step 302 and gets the next frame. If tracking was unsuccessful the detection process of FIG. 2 is performed again in step 308.

Figure 4:
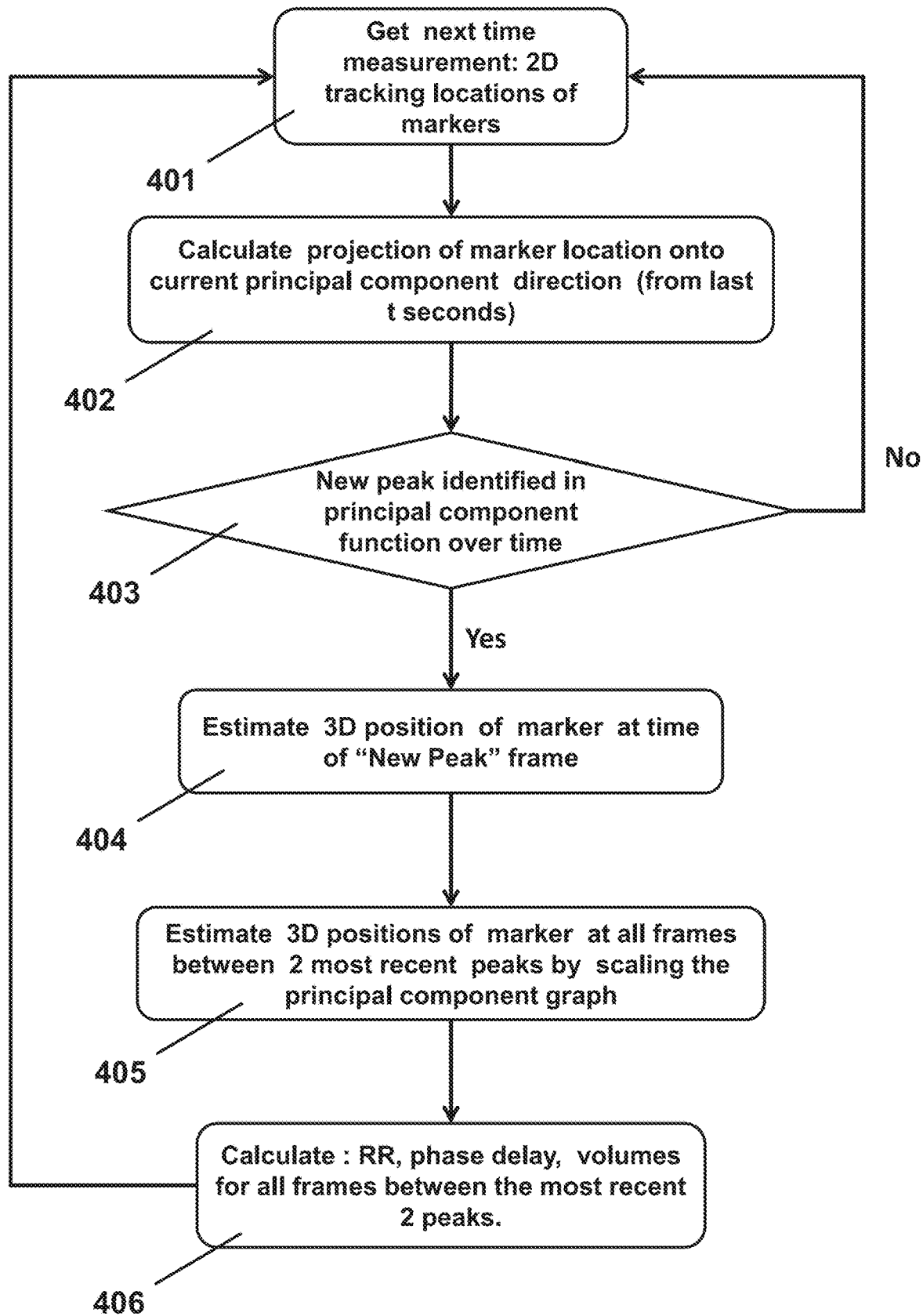
FIG. 4 is a flow chart of an analysis stage, according to one embodiment of the invention.

FIG. 4 is a flowchart of the analysis process. In this process would begin by getting 2D tracking locations of markers, in step 401. Step 402 calculates the projection of marker location onto the current principal component direction from the last t seconds. If a new peak is identified in the principal component function over time, in step 403, the 3D position of the marker at the time of "New Peak" frame is estimated in step 404; else, step 401 is repeated. The 3D position of the marker at all frames between the two most recent peaks is estimated by scaling the principal component graph in step 405 and the RR, phase delay and the volumes for all frames between the most recent two peaks is calculated in step 406, after which the process restarts at step 401.

Figure 5:
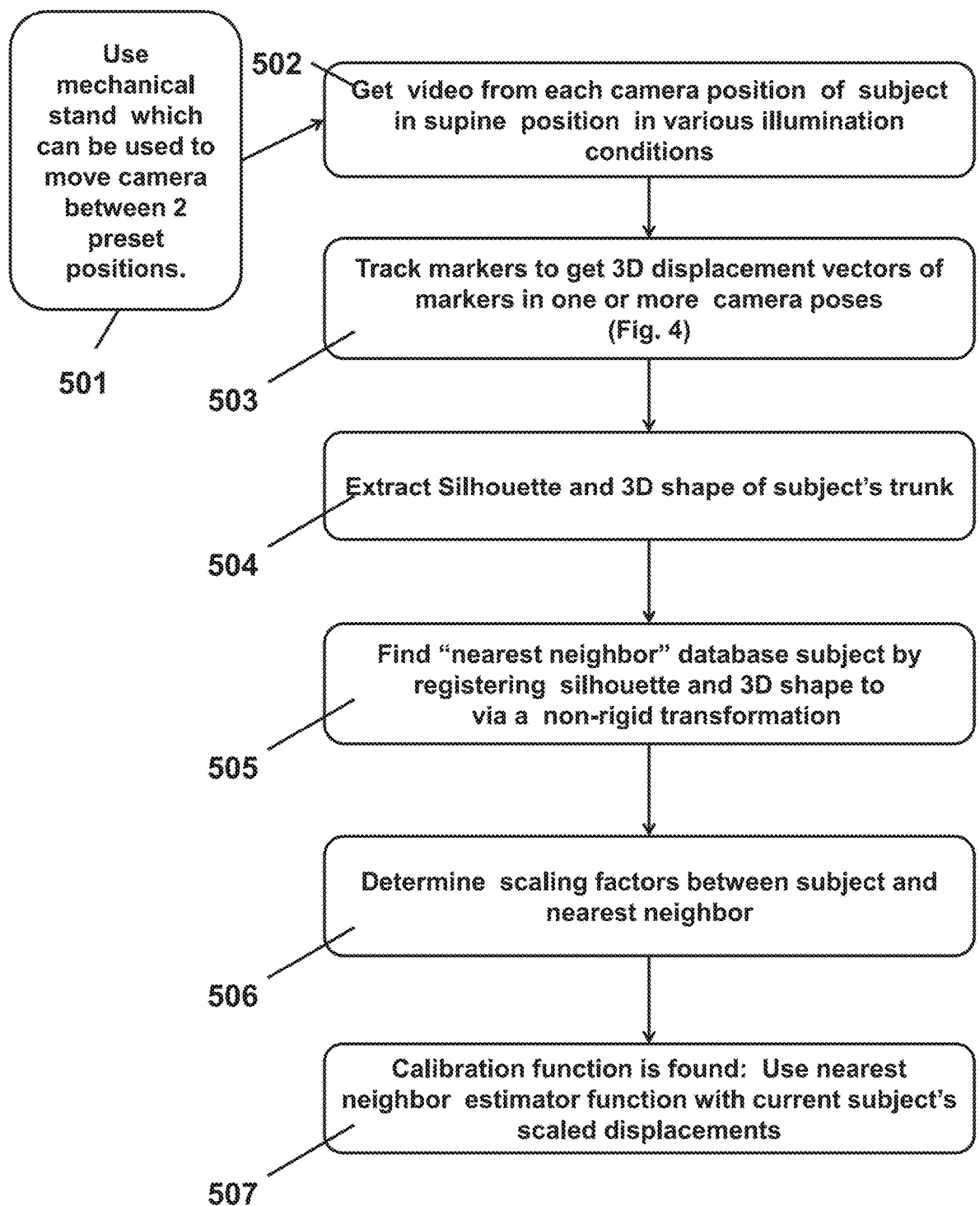
FIG. 5 is a flow chart of a volume calibration stage, according to one embodiment of the invention.

FIG. 5 is a flowchart of a volume calibration procedure that may be carried out according to some embodiments of the invention. The calibration process begins in step 501 where mechanical calibration is performed. Then, in step 502, the subject is recorded from each camera in supine position in various illumination conditions. In step 503 the marker's position on the subject are tracked to obtain 3-D displacement vectors, and in step 504 the silhouette and the 3D shape of the subject's trunk is extracted. In step 505 the "nearest neighbor" database subject is found by registering the silhouette and the 3D shape via a non-rigid transformation. In step 506 the scaling factor between the subject and his nearest neighbor is determined. The calibration function is found in step 507 by using the nearest neighbor estimator function with the current subject's scaled displacement.

Illustrative Markers

Figure 6:
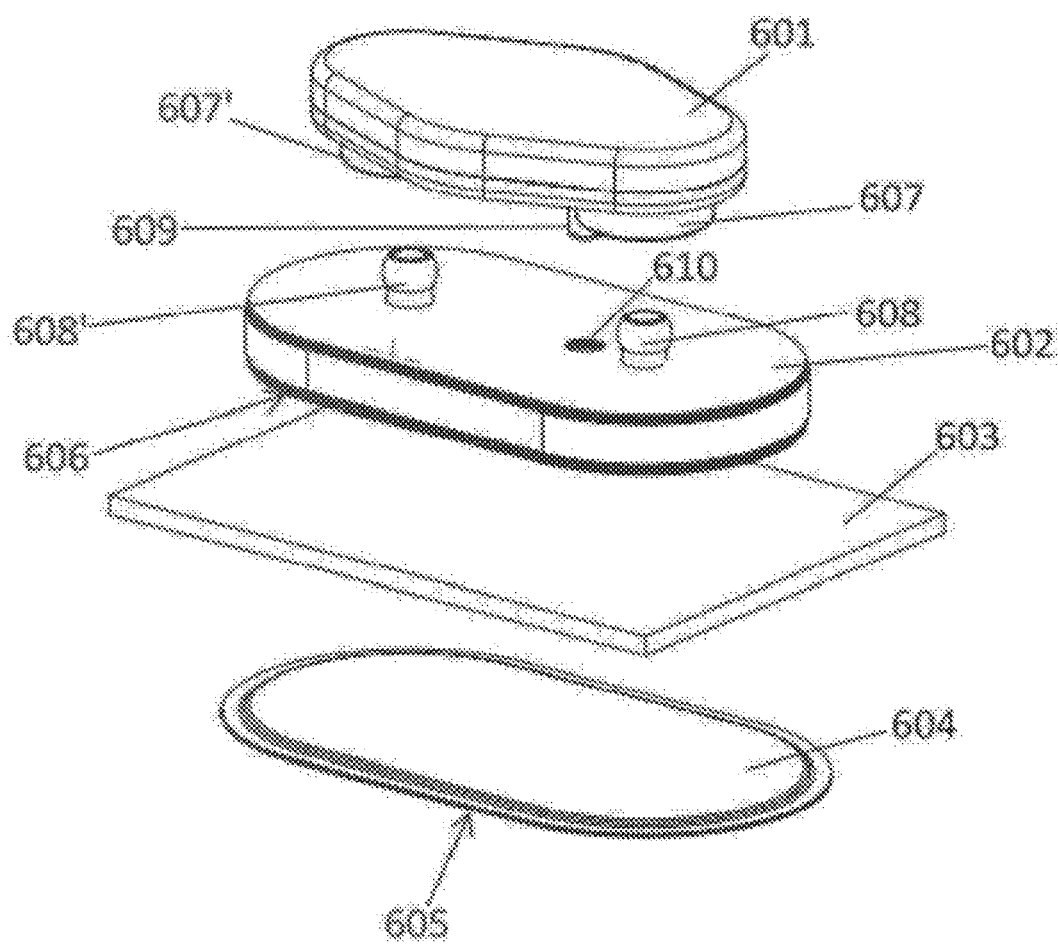
FIG. 6 shows a marker according to one embodiment of the invention in separated position relative to a cloth, as may be part of the subject's robe.

FIG. 6 illustrates the main parts of a marker according to one embodiment of the invention, consisting of LED assembly 601, which contains a LED, together with circuitry needed to operate it. Operating LED's is conventional in the art and is well known to the skilled person and therefore said circuitry is not shown in detail, for the sake of brevity. Assembly 601, in this embodiment of the invention, is meant for multiple uses and operates together with disposable part 602, which in some embodiments of the invention is applied directly to the subject's skin, e.g. using an adhesive surface provided at its bottom. In the embodiment of FIG. 6, however, disposable part 602 is located above a fabric 603, which may be, for instance, a subject's pajama or a blanket, and is kept in position relative to said fabric by a lower base 604, which is maintained in position on the subject's body by using an adhesive material located on its bottom 605. Lower base 604 can be coupled to the bottom 606 of disposable part 602 in a variety of ways, e.g. by magnetic coupling between the two, or by providing mechanical coupling, e.g., through pins that perforate and pass through fabric 603 (not shown).

As will be described in greater detail with reference to FIG. 10, disposable part 602 may contain batteries needed to operate the LED, as well as, if desired, additional circuitry. Reusable LED assembly 601 is connected to disposable part 602 through seats 607 and 607', which engage buttons 608 and 608' located in disposable part 602. An additional positioning pin 609 can be provided in LED assembly 601, to engage hole 610 in disposable part 602. Electrical contact can be provided from the power supply located in disposable part 602, through buttons 608 and 608', although of course many alternative ways exist of conveying power from the batteries to the LED assembly 601.

Figure 7:
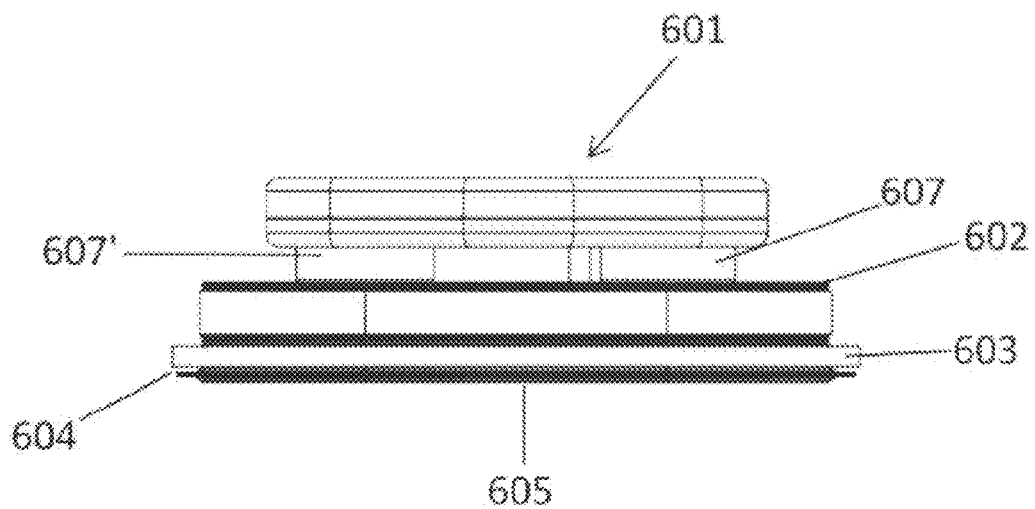
FIG. 7 shows the marker of FIG. 6 in operating position.
Figure 8:
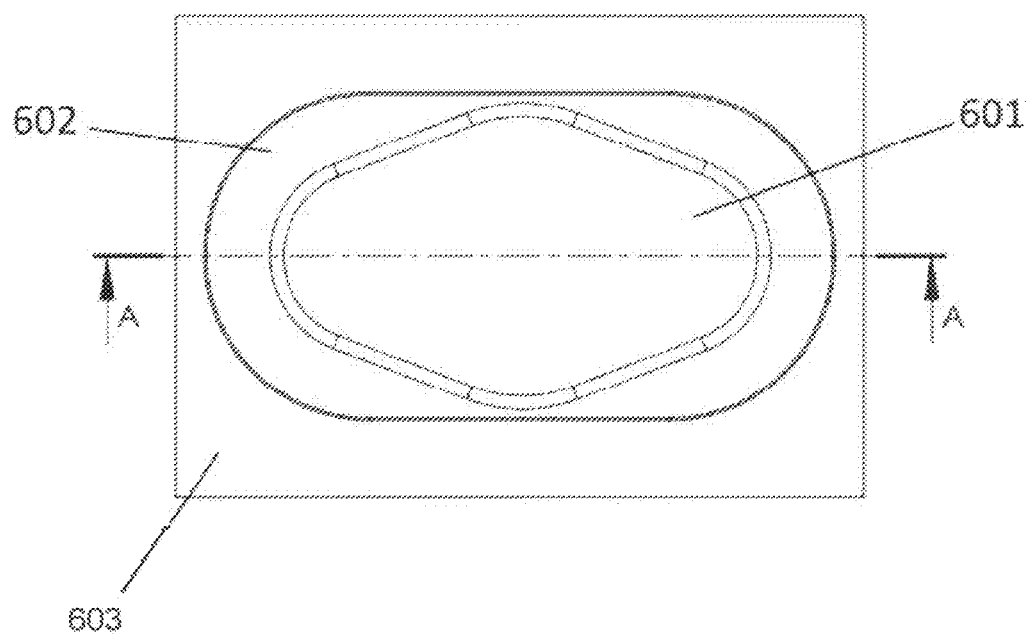
FIG. 8 is a top view of the marker of FIG. 7.
Figure 9:
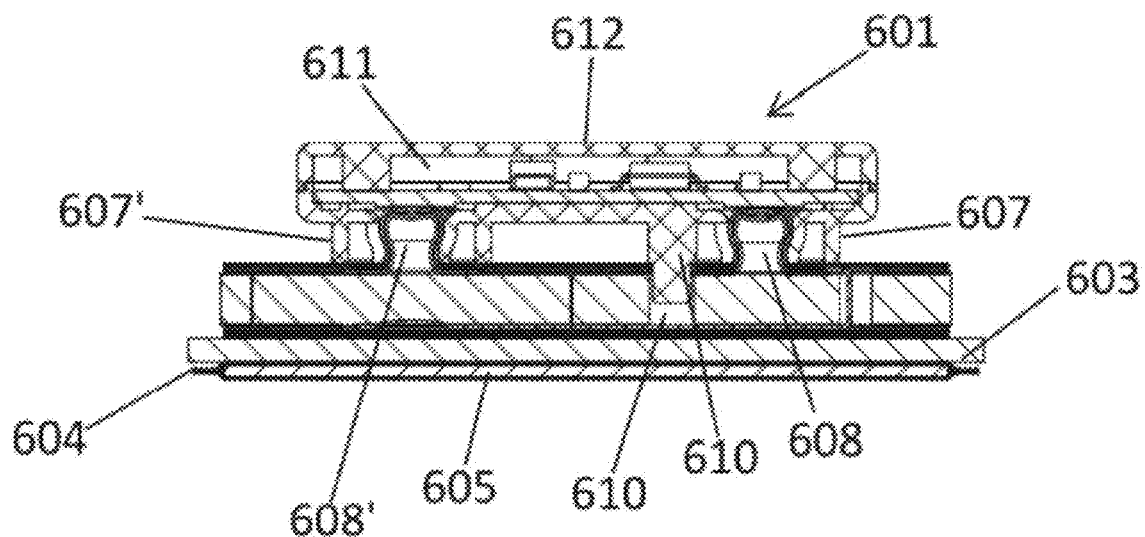
FIG. 9 is a cross-section taken along the AA line of FIG. 8.

FIG. 7 is an operationally connected view of the various elements of FIG. 6, the same numerals being used to indicate the same parts. FIG. 8 is a top view of the assembled marker devise of FIG. 7, and FIG. 9 is a cross-section of the same device assembly, taken along the AA line of FIG. 8. In this cross-section, in addition to the elements already described above a compartment 611 is seen, which houses the LED, as well as electronics used to operate it. Of course, the top portion 612 of LED assembly 601 is made of material of a transparency sufficient to allow the required amount of light generated by the LED to be viewed from the outside.

Figure 10:
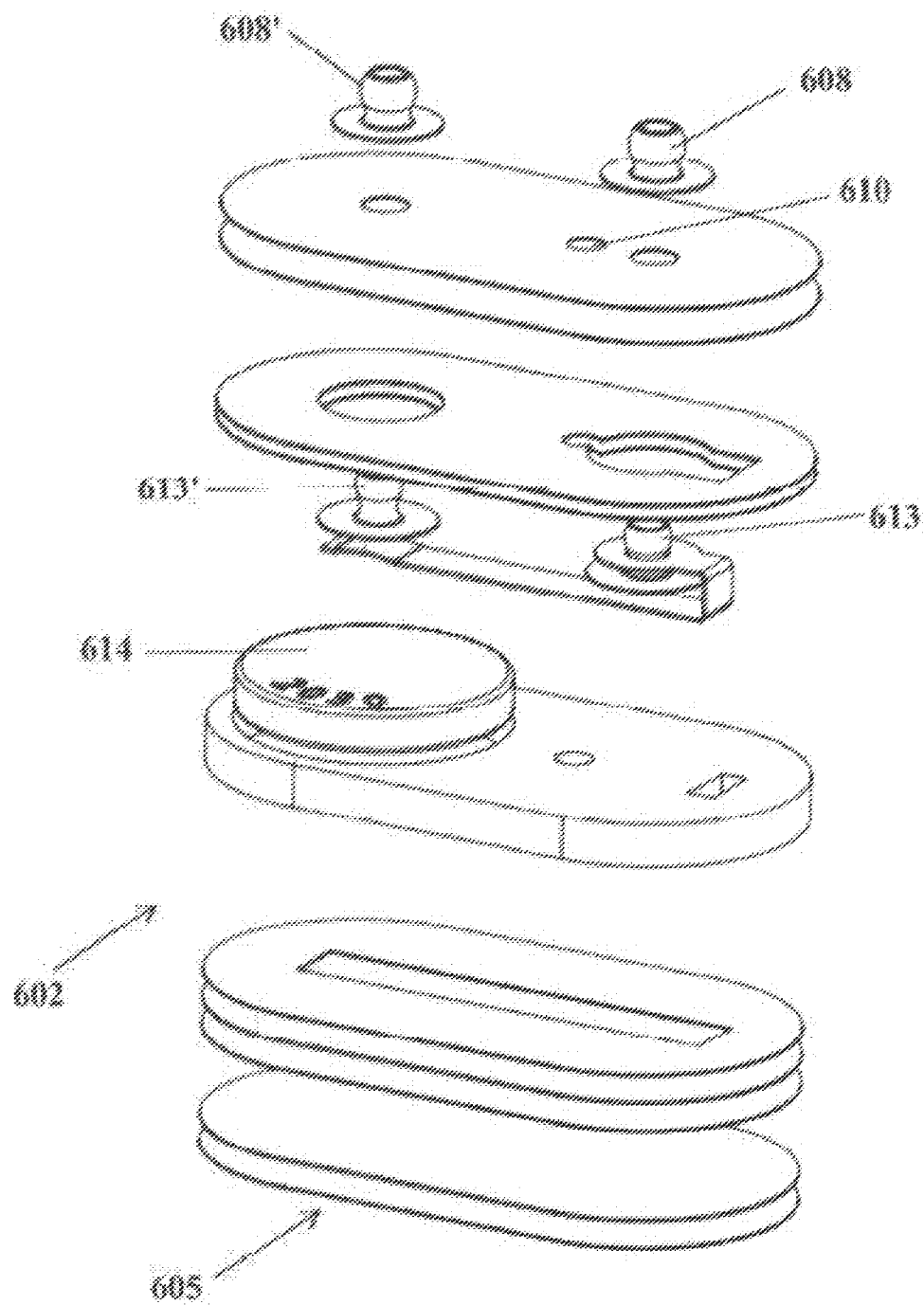
FIG. 10 is an exploded view of the disposable part of a marker according to one embodiment of the invention.

FIG. 10 shows the disposable part 602 of FIGS. 6-9 in exploded view. This disposable assembly is made of a plurality of elements and layers, kept together by gluing or by mechanical connection, for instance when upper buttons 608 and 608' are connected with a lower buttons 613 and 613'. A battery 614 is provided as the power supply to the LED assembly, which can be, for instance, a standard 2030 disc battery.

As will be apparent to the skilled person the arrangement of the disposable assembly 602, as well as that of the LED assembly 601 provided in the figures, represents only one of countless possible arrangements and is provided only for the purpose of illustration. Additionally, Multi-LED assemblies can be devised by the skilled person, to provide two or more LEDs in the same LED assembly, while performing the required dimensional changes. Such alternatives and modifications are clear to the skilled person from the above description and, therefore, are not further described in detail, for the sake of brevity.

All the above description of markers, methods, uses, etc. have been provided for the purpose of illustration and are not intended to limit the invention in any way. Many modifications, alternative configurations, process steps and methods can be provided by the skilled person, without exceeding the scope of the invention.

The invention claimed is:
1. A method for monitoring respiratory characteristics of a subject, comprising:
 a) applying one or more movement sensors comprised in one or more markers to a thorax and/or an abdomen of the subject, for generating first signals which represent one or more rotations of said one or more movement sensors, that are indicative of the respiratory characteristics of said subject;
b) receiving said first generated signals during breathing motion of said subject by a receiver; and
c) analyzing said first generated signals by one or more computing devices which are in data communication with said receiver;
wherein said one or more computing devices:
i. generate a first breathing pattern from said first signals;
ii. divide each respiratory cycle experienced by said subject and defined by said first breathing pattern into a plurality of portions, each of said plurality of portions delimited by two different time points and calculate, for each of said plurality of portions of a given respiratory cycle of said first breathing pattern, a slope representing a thorax and/or abdomen movement; and
iii. compare between corresponding calculated slopes of said portions of said first breathing pattern with estimated pulmonary air flow rates during different phases of the respiratory cycle, to calibrate the thorax movements of said subject; and
iv. determine respiratory characteristics of said subject for subsequent respiratory cycles experienced by said subject, based on said calculated thorax movements and said calibration.

2. The method of claim 1, wherein said generated first signals include data of said one or more rotations of said one or more markers, said data including inclination angles of said movement sensors to gravity.

3. The method of claim 1, further comprising applying one or more additional movement sensors to a body of the subject, for generating third signals, said third signals indicative of movement of the abdomen of the subject, wherein the receiver receives said third signals during the breathing motion of said subject and the one or more computing devices generates a third breathing pattern from said third signals and divides each respiratory cycle experienced by the subject and defined by said third pattern into a plurality of portions, such that a portion of said third pattern is delimited by the same two time points as a corresponding portion of the first pattern.

4. The method of claim 3, wherein the one or more computing devices calculate, for each of the plurality of portions of a given respiratory cycle of the third pattern, a slope representing the abdomen movement and determines respiratory characteristics of the subject for subsequent respiratory cycles based on the calculated thorax movements and the abdomen movements.

5. The method of claim 4, wherein the determined respiratory characteristics include identification of full and/or partial breathing obstruction.

6. The method of claim 3, wherein each of the one or more movement sensors and the one or more additional movement sensors comprises an accelerometer, a gyroscope, or a combination thereof.

7. The method of claim 3, wherein each of the one or more movement sensors is positionable on a fabric located in engagement with the subject's thorax, and is further provided with fastening means adapted to maintain said movement sensor in a desired positional relationship to a chosen location on the subject's thorax, and wherein each of the one or more additional movement sensors is positionable on a fabric located in engagement with the subject's abdomen, and is further provided with fastening means adapted to maintain said additional movement sensor in a desired positional relationship to a chosen location on the subject's abdomen.

8. The method of claim 1, further comprising applying an alarming device which is in data communication with said one or more computing devices, wherein the one or more computing devices commands said alarming device to generate an alert if said first generated signals exceed a predetermined threshold.

9. The method of claim 1, wherein the one or more computing devices readjusts the calibration of said slopes with said estimated pulmonary air flow rates during the course of the breathing motion.

10. The method of claim 1, further comprising attaching one or more straps for said one or more movement sensors to a body of the subject, to facilitate performance of a breathing motion measuring operation.

11. The method of claim 1, wherein the one or more computing devices is provided with communication apparatus suitable to deliver raw or analyzed data to a remote device.

12. The method of claim 1, wherein the determined respiratory characteristics include tidal volume.

13. The method of claim 1, further comprising applying one or more LEDs comprised in one or more markers to the body of the subject, for generating respiratory signals, said respiratory signals indicative of movement of the thorax and/or of the abdomen of the subject.

14. The method of claim 13, wherein the receiver is configured to receive said first generated signals during the breathing motion of said subject and the one or more computing devices generates a pattern from said respiratory signals and compares a selected portion of said pattern with a selected portion of the said first breathing pattern.

15. The method of claim 14, wherein the compared selected portion of said pattern from said respiratory signals and the selected portion of said first breathing pattern include tidal volume.

16. The method of claim 1, wherein the determined respiratory characteristics include identification of non-breathing motion epochs.

17. A system for monitoring respiratory characteristics of a subject, comprising:
a) one or more movement sensors, applied to a thorax and/or an abdomen of the subject, for generating signals that are indicative of the respiratory characteristics of said subject;
b) a receiver for receiving said generated signals during breathing motion of said subject; and
c) one or more computing devices in data communication with said receiver;
wherein said one or more computing devices is operable to:
i. generate a pattern from said signals;
ii. divide each respiratory cycle into a plurality of portions, each of said portions delimited by two different time points, and calculate, for each portion of a given respiratory cycle, a pattern and a slope representing a thorax movement; and
iii. compare between corresponding calculated slopes of said portions of said given respiratory cycle with estimated pulmonary air flow rates during different phases of the respiratory cycle, to calibrate the thorax movements of said subject; and iv. determine respiratory characteristics of said subject for subsequent respiratory cycles experienced by said subject, based on said calculated pattern and slope and said calibration.

18. The system of claim 17, in which the respiratory characteristics of said subject are updated, based on detection of changes in rotation angles of said one or more movement sensors.

19. The system of claim 17, wherein the one or more computing devices readjust the comparison of said slopes with said estimated pulmonary air flow rates during the course of the comparison.

20. The system of claim 17, wherein each of the one or more movement sensors comprises an accelerometer, a gyroscope, or a combination thereof.

* * * * *